(12) United States Patent
    Cho et al.

(10) Patent No.: US 9,585,945 B2
(45) Date of Patent: Mar. 7, 2017

(54) COMPOSITION FOR PREVENTING OR TREATING AUTOIMMUNE DISEASE, COMPRISING, AS ACTIVE INGREDIENT, PINK1 PROTEIN OR POLYNUCLEOTIDE ENCODING SAME

(71) Applicant: CATHOLIC UNIVERSITY INDUSTRY ACADEMIC COOPERATION FOUNDATION, Seoul (KR)

(72) Inventors: Mi-La Cho, Seoul (KR); Hyang-Suk Rhim, Seoul (KR); Seon-Yeong Lee, Gyeonggi-do (KR); Yeong-Mi Mun, Seoul (KR); Hye-Jin Son, Seoul (KR); Eun-Ji Yang, Seoul (KR); Eun-Kyung Kim, Seoul (KR)

(73) Assignee: CATHOLIC UNIVERSITY INDUSTRY ACADEMIC COOPERATION FOUNDATION, Seoul (KR)

( * ) Notice: Subject to any disclaimer, the term of this patent is extended or adjusted under 35 U.S.C. 154(b) by 0 days.

(21) Appl. No.: 14/948,095

(22) Filed: Nov. 20, 2015

(65) Prior Publication Data
    US 2016/0114007 A1    Apr. 28, 2016

Related U.S. Application Data

(63) Continuation-in-part of application No. PCT/KR2014/002457, filed on Mar. 24, 2014.

(30) Foreign Application Priority Data

May 22, 2013 (KR) .................. 10-2013-0057659

(51) Int. Cl.
    *C12N 9/12*     (2006.01)
    *A61K 48/00*    (2006.01)
    *A61K 38/45*    (2006.01)

(52) U.S. Cl.
    CPC .......... *A61K 38/45* (2013.01); *A61K 48/005* (2013.01); *C12N 9/12* (2013.01); *C12Y 207/11001* (2013.01)

(58) Field of Classification Search
    CPC .......... A61K 38/45; A61K 38/48; C12N 9/12
    See application file for complete search history.

(56) References Cited

FOREIGN PATENT DOCUMENTS

KR    2011-0125495    11/2011

OTHER PUBLICATIONS

Wilhemus et al. 2012; Involvement and interplay of Parkin, PINK1, and DJ1 in neurodegenerative and neuroinflammatory disorders. Free Radical Biology and Medicine. 53: 983-992.*
Ellis et al. 2013; Mitochondrial and cytosolic roles of PINK1 shape induced regulatory T-cell development and function. European Journal of Immunology 43: 3355-3360.*
Motoko Unoki and Yusuke Nakamura, "Growth-suppressive e.ects of BPOZ and EGR2, two genes involved in the PTEN signaling pathway," Oncogene (2001) 20, 4457-4465.
GenBank: BAB55651.1, "PTEN induced putative kinase 1 [Mus musculus]".
GenBank: AB053476.1, "Mus musculus PINK1 mRNA for PTEN induced putative kinase 1, complete cds".
Vural et al., Seroreactivity against PTEN-induced putative kinase 1 (PINK1) in Turkish patients with Behçet's disease, Clin Exp Rheumatol 2009: 27 (Suppl. 53):S67-S72.
PCT/KR2014/002457, Mar. 24, 2014, Search Report.

* cited by examiner

*Primary Examiner* — Karen Cochrane Carlson
(74) *Attorney, Agent, or Firm* — Joseph Hyosuk Kim; JHK Law

(57) ABSTRACT

The present invention relates to a composition for preventing or treating an autoimmune disease comprising, as an active ingredient, PINK1 protein or polynucleotide encoding the same. The PINK1 protein according to the present invention inhibits the activity of Th17, promotes the activity of a regulatory T cell (Treg), and increases autophagy in Treg cells, thereby controlling excessive immune responses. Therefore, the PINK1 protein can be effectively used as a pharmaceutical composition or an immunosuppressant, which is capable of preventing or treating an autoimmune disease, such as arthritis, and the like, caused by dysregulation of various kinds of immune responses.

10 Claims, 16 Drawing Sheets

COMPOSITION FOR PREVENTING OR TREATING AUTOIMMUNE DISEASE, COMPRISING, AS ACTIVE INGREDIENT, PINK1 PROTEIN OR POLYNUCLEOTIDE ENCODING SAME

TECHNICAL FIELD

The present invention relates to a composition for preventing or treating an autoimmune disease comprising, as an active ingredient, PTEN-induced kinase 1 (PINK1) protein or polynucleotide encoding the same.

BACKGROUND ART

Immunity is one of self-protection systems in vivo against all external polymers (antigens) which are invaded or injected into tissues. A lymphocyte as a major component of an immune system is a leukocyte which is generated in the bone marrow and circulated in a lymph tissue or organ, particularly, a lymphatic node, a spleen, and onsil along the blood. As cells involved in an immune response, B cells are rapidly proliferated when being stimulated by a proper antigen to form a clone which makes a specific antibody (immunoglobulin) for neutralizing the antigen and the antibody made by the B cell performs the humoral immunity while circulating in the body fluid. Further, T cells are generated in the thymus to move to a lymphatic tissue and are responsible for cell-mediated immunity to directly attack the antigen.

Meanwhile, in all normal objects, one of the important features has ability capable of detecting, respond, and removing many non-self antigens without harmfully responding to self-antigen substances. As such, non-response to the self-antigen of the living body is called immunologic unresponsiveness or tolerance.

When a problem is caused in inducing or continuously maintaining the self-tolerance, the immune response to the self-antigen occurs. As a result, a phenomenon in which the self-antigen attacks the self-tissue occurs to cause autoimmune diseases such as multiple sclerosis, type 1 diabetes, rheumatoid arthritis, and Hashimoto's thyroiditis and cause immune rejection after a surgical procedure such as transplantation.

In detail, since the autoimmune disease is a disease caused by abnormal response to self-cells, drugs which suppress an autoimmune function have been mainly used for treatment. However, the drugs have many side effects to be difficult to be continuously used and do not sufficiently prevent a recurrence to have a limit in the treatment for a full recovery. In the case of multiple sclerosis, beta interferon is used, but the beta interferon has expensive treatment cost instead of less side effects and inconvenience in that an injection is required during life, and has a slight effect of preventing the recurrence. Further, a method of inhibiting interaction between cells by administrating an antibody to a CD40 ligand has been used, but is not so successful. Other many immune therapies are included, but there is yet no case admitted as a method which exhibits clear therapeutic efficacy.

Accordingly, the autoimmune disease may be efficiently treated and researches of therapeutic agents which are harmless to the human body and have no side effect are required.

DISCLOSURE

Technical Problem

Therefore, the inventors completed the present invention by verifying the fact that a PINK1 protein inhibits the activity of Th17, promotes the activity of a regulatory T cell (Treg), and increases autophagy in Treg cells to control the Treg function, thereby efficiently treating autoimmune diseases, while studying a new treating method capable of efficiently preventing and treating the autoimmune diseases.

Therefore, an object of the present invention is to provide a composition for preventing or treating an autoimmune disease comprising PINK1 protein as an active ingredient.

Further, another object of the present invention is to provide a composition for preventing or treating an autoimmune disease comprising, as an active ingredient, polynucleotide encoding the PINK1 protein or a recombinant vector bound to operate the polynucleotide.

Technical Solution

An aspect of the present invention provides a composition for preventing or treating an autoimmune disease comprising, as an active ingredient, PINK1 protein.

In the exemplary embodiment of the present invention, the PINK1 protein may have an amino acid sequence represented as SEQ ID NO: 1.

In the exemplary embodiment of the present invention, the PINK1 protein may inhibit or decrease the activity of Th17 or promote or increase the activity of a regulatory T cell (Treg).

In the exemplary embodiment of the present invention, the PINK1 protein may decrease differentiation of osteophage or inhibit infiltration of inflammatory cells.

Further, another aspect of the present invention provides a composition for preventing or treating an autoimmune disease comprising, as an active ingredient, polynucleotide encoding the PINK1 protein.

In an exemplary embodiment of the present invention, the polynucleotide may have a base sequence represented as SEQ ID NO: 2.

Further, yet another aspect of the present invention provides a pharmaceutical composition for preventing or treating an autoimmune disease comprising, as an active ingredient, a recombinant vector bound to operate the polynucleotide encoding the PINK1 protein.

In an exemplary embodiment of the present invention, the autoimmune disease may be selected from a group comprised of rheumatoid arthritis, systemic lupus erythematosus, digestive diabetes, atopic dermatitis, autoimmune encephalomyelitis, asthma, and Crohn's disease.

Still another aspect of the present invention provides a composition for preventing or treating autoimmune disease comprising, as an active ingredient, PINK1 protein.

It is known that the PINK1 protein as a gene of autosomal recessive familiar PD is expressed in both nerve cells and gliocyte, and has an effect on preventing diseases such as cancer and type 1 diabetes, but a document in which the PINK1 protein is used in the treatment of the autoimmune diseases is so far not been known at all.

Accordingly, the inventors first established that the PINK1 protein has an effect on controlling the Treg function by increasing autophagy in Treg cells.

Such a result may be verified by an exemplary embodiment of the present invention, and in order to examine whether the PINK1 protein has an effect on preventing and treating arthritis, in an arthritis model, as a result of measuring an arthritis index and a disease severity index, it could be seen that as compared with a control group without treating the PINK1 protein, in an experimental animal group in which the PINK1 protein of the present invention is administrated, the arthritis index and the disease severity index are significantly suppressed and in lymphatic gland cells of a PINK1 injection group, the proliferation activity of T cells is inhibited (see FIGS. 1A and 1B).

According to another exemplary embodiment of the present invention, in order to analyze the improved degree of arthritis according to PINK1 protein treatment, as a result of carrying out a histological inspection by staining hematoxylin and eosin and staining toluidin blue and safranin O, the joint of the control group without treating the PINK1 protein is broken and inflammatory cells are infiltrated. However, it could be seen that in the experimental animal group in which the PINK1 protein is injected, as compared with the control group, the differentiation of osteophage is decreased and further, the infiltration of the inflammatory cells is suppressed (see FIGS. 2A and 2B).

According to another exemplary embodiment of the present invention, as a result of analyzing expression of inflammatory cytokines in the articular tissue according to the treatment of the PINK1 protein, in the articular tissue of the PINK1 injection group of the present invention, the expression of inflammatory cytokines such as IL-17, IL-6, IL-1b, and TNF-α is significantly inhibited as compared with the control group, and the result suggests that the PINK1 protein may control the activity of the inflammatory cytokines in an autoimmune arthritis disease (see FIG. 3).

According to another exemplary embodiment of the present invention, in order to verifying an effect of simultaneously controlling Th17 and the Treg cell according to the treatment of the PINK1 protein, as a result of implementing a fluorescence-activated cell sorter (FACS) in the splenocytes of an arthritis mouse animal model, in the group in which the PINK1 protein is injected, the Th17 cells is decreased by more than half and the Treg cells are increased almost two times (see FIGS. 4A and 4B), and form this, it can be seen that the PINK1 protein may simultaneously control the activity of the Th17/Treg cells.

According to another exemplary embodiment of the present invention, in the arthritis animal model, as a result of verifying an effect on inhibiting the Th17 cells due to the PINK1 protein treatment, as compared with the arthritis animal model as the control group, the Th17 cells which are pathologic cells are significantly inhibited in the spleen of the mouse treated with the PINK1 protein, expression of RORrT genes which are transcription factors of the Th17 cells are suppressed, and further, expression of phosphorylated STAT3 which is the transcription factor of the Th17 cell is significantly suppressed in the PINK1 injection group (see FIGS. 5A to 5C). The result shows that the PINK1 protein may control the activity of RORrT and STAT3 when suppressive-controlling the activity of the Th17 cell.

According to another exemplary embodiment of the present invention, in the arthritis animal model, as a result of verifying an effect on an increase in Treg cells by the PINK1 protein treatment, as compared with the arthritis animal model as the control group, expression of the Treg cells which are pathologic cells are significantly suppressed in the spleen of the mouse treated with the PINK1 protein, expression of Foxp3 and SOCS3 genes which are representative transcription factors of the Treg cells are increased, and further, expression of phosphorylated STAT5 which is the transcription factor of the Treg cell is significantly increased in the PINK1 injection group (see FIGS. 6A to 6C).

According to another exemplary embodiment of the present invention, as a result of verifying an inhibitory regulation effect of inflammatory cytokines by transfection in vitro of the PINK1 gene, in the cell injected with the PINK1 gene, the expression of TNF-α according to a conA response is significantly suppressed (see FIG. 7). From this, even in an efficacy evaluation in vitro, it can be seen that the PINK1 protein may directly control the expression of inflammatory cytokines.

Furthermore, according to another exemplary embodiment of the present invention, as a result of observing autophagy expressed in the Th17 and Treg cells through a confocal microscope in a group which is injected with the PINK1 protein and a control group which is not injected with the PINK1 protein in the splenocyte of the mouse, as compared with the Th17 cells, it can be seen that in the splenocyte Treg cells of the mouse injected with the PINK1 protein, the expression of LC3 and coxIV is increased and further, markers of the Treg cells are activated (see FIG. 8).

Accordingly, based on the fact verified through the exemplary embodiment of the present invention in addition to such a known fact, it can be seen that the PINK1 protein of the present invention may be used for preventing or treating autoimmune disease by increasing the autophagy in Treg cells to control the Treg function.

Therefore, the PINK1 protein or the polynucleotide encoding the protein of the present invention have the activity of increasing the autophagy in Treg cells to prevent or treat the autoimmune disease through an action of promoting or increasing the activity or the expansion of the regulatory T (Treg) cells.

In the present invention, the term "activity" means that all mechanisms of the regulatory T cells in vivo, that is, the Treg cells including natural Treg and adaptive Treg cells are promoted or enhanced and that an immunoregulatory action, for example, an immunosuppressive action is promoted or enhanced so as to maintain a normal state of the immune response in vivo.

Further, in the present invention, the expression of "expansion" means that undifferentiated T cells are differentiated and proliferated to the Treg cells and "differentiation" means that while cells are divided and proliferated and grown, structures or functions thereof are specified, that is, forms or functions are changed so that cells, tissues, and the like of an organism perform respective given operations, and "proliferation" means that the cells are divided and thus homogenous cells are increased, and generally, the number of cells in the body of a multicellular organism.

The PINK1 protein according to the present invention may be preferably a protein having an amino acid sequence expressed by SEQ ID NO: 1. Further, the PINK1 protein of the present invention may be a functional equivalent for polypeptide having an amino acid sequence expressed by SEQ ID NO: 1. In the present invention, the term "functional equivalent" means polypeptide or protein having sequence homology of at least 60%, preferably 70%, and more preferably 80% or more with the amino acid sequence represented as SEQ ID NO: 1 as a result of addition, substitution, or deletion of amino acid and means polypeptide having the substantially homogenous activity with the PINK1 protein. Here, the "substantially homogenous activity" means the activity of the PINK1 protein disclosed above. In the functional equivalent, amino acid sequence variants in which a part of the amino acid having the amino acid sequence represented as SEQ ID NO: 1 is substituted, deleted, or added may be included. The substitution of amino acids is preferably a conservative substitution. Examples of conservative substitutions of amino acids present in nature are as follows; aliphatic amino acids (Gly, Ala, Pro), hydrophobic amino acids (Ile, Leu, Val), aromatic amino acids (Phe, Tyr, Trp), acidic amino acids (Asp, Glu), basic amino acids (His, Lys, Arg, Gln, Asn) and sulfur-containing amino acids (Cys, Met). The deletion of amino acids may be preferably located in the part which is not directly involved in the activity of the PINK1 protein. Further, in the range of the functional equivalent, a polypeptide derivative in which a partial chemical structure of polypeptide is modified while maintaining a basic skeleton of the PINK1 protein and its physiological activity may be included. For example, a fusion protein created by fusion with other proteins and the like may be included in the functional equivalent while maintaining the structural modification and the physiological activity for modifying stability, storage, volatility, solubility, or the like of polypeptide of the present invention.

The PINK1 protein or the polynucleotide encoding the protein according to the present invention may decrease or inhibit the Th17 cells as the pathological cells, while may prevent or treat autoimmune disease through an action of promoting or enhancing the activity or the expansion of the regulatory T cell.

In the present invention, the "autoimmune disease" means a disease caused by such a process that when a problem in inducing or continuously maintaining the tolerance occurs, the immune response to the self-antigen occurs, and thus a phenomenon in which the self-antigen attacks its tissue occurs. Further, in the present invention, a kind of autoimmune disease is not limited thereto, but may be selected from a group comprised of rheumatoid arthritis, systemic lupus erythematosus, digestive diabetes, atopic dermatitis, autoimmune encephalomyelitis, asthma, and Crohn's disease.

In the present invention, the term 'treatment' means that a disease or a disorder or one or more symptoms of the disease or the disorder to which the term is applied is reversed or alleviated or the progress thereof is inhibited or prevented, and the term 'treatment' used in the present invention means a treating action when the "treating" is defined as described above.

The pharmaceutical composition for preventing or treating the autoimmune disease according to the present invention may include a PINK1 protein with a pharmaceutically effective amount alone or include one or more carriers, excipients, or diluents which are pharmaceutically acceptable. The pharmaceutically effective amount means an amount sufficient to prevent, improve, and treat symptoms of the autoimmune disease. The pharmaceutically effective amount of the PINK1 protein according to the present invention is 0.5 to 100 mg/day/weight kg and preferably 0.5 to 5 mg/day/weight kg. However, the pharmaceutically effective amount may be properly changed according to the degree of the symptom of the autoimmune disease, and an age, a weight, a health state, a sex, an administration route, and a treatment period of a patient, and the like.

Further, the expression of "pharmaceutically acceptable" generally means a composition which does not cause an allergic reaction such as gastroenteric trouble and dizziness or a similar reaction thereto when being physiologically acceptable and administrated to the human body. Example of the carriers, the excipients, and the diluents may include lactose, dextrose, sucrose, sorbitol, mannitol, xylitol, erythritol, maltitol, starch, acacia rubber, alginate, gelatin, calcium phosphate, calcium silicate, cellulose, methyl cellulose, polyvinylpyrrolidone, water, methyl hydroxybenzoate, propyl hydroxybenzoate, talc, magnesium stearate, and mineral oil. Further, a filler, an anti-coagulant, a lubricant, a wetting agent, a perfume, an emulsifier, a preservative, and the like may be additionally added.

Further, the composition of the present invention may be formulated by using a known method in the art so as to provide rapid, sustained, or delayed release of an active component after being administrated to the mammal. The formulation may be a form of a powder, granules, a tablet, an emulsion, syrup, an aerosol, a soft or hard gelatin capsule, a sterile injection solution, and a sterile powder.

Further, the composition for preventing or treating the autoimmune disease according to the present invention may be administrated through various routes including oral, percutaneous, subcutaneous, intravenous and intramuscular tissues, and the administration amount of the active component may be properly selected according to various factors such as an administration route, an age, a sex, and a weight of a patient, and the severity of the patient. The composition for preventing or treating the autoimmune disease according to the present invention may be administrated by combining a known compound having an effect of preventing, improving, or treating the symptom of the autoimmune disease.

Further, the present invention may provide a pharmaceutical composition for preventing or treating autoimmune disease comprising the PINK1 protein as an active ingredient, and furthermore, the present invention may provide an immunosuppressant comprising the PINK1 protein as an active ingredient.

Advantageous Effects

The PINK1 protein according to the present invention inhibits the activity of Th17, promotes the activity of a regulatory T cell (Treg), and increases autophagy in Treg cells, thereby controlling excessive immune responses. Therefore, the PINK1 protein can be effectively used as a pharmaceutical composition or an immunosuppressant, which is capable of preventing or treating an autoimmune disease, such as arthritis, and the like, caused by dysregulation of various kinds of immune responses.

SEQUENCE LISTING FREE TEXT

Figure 1A:
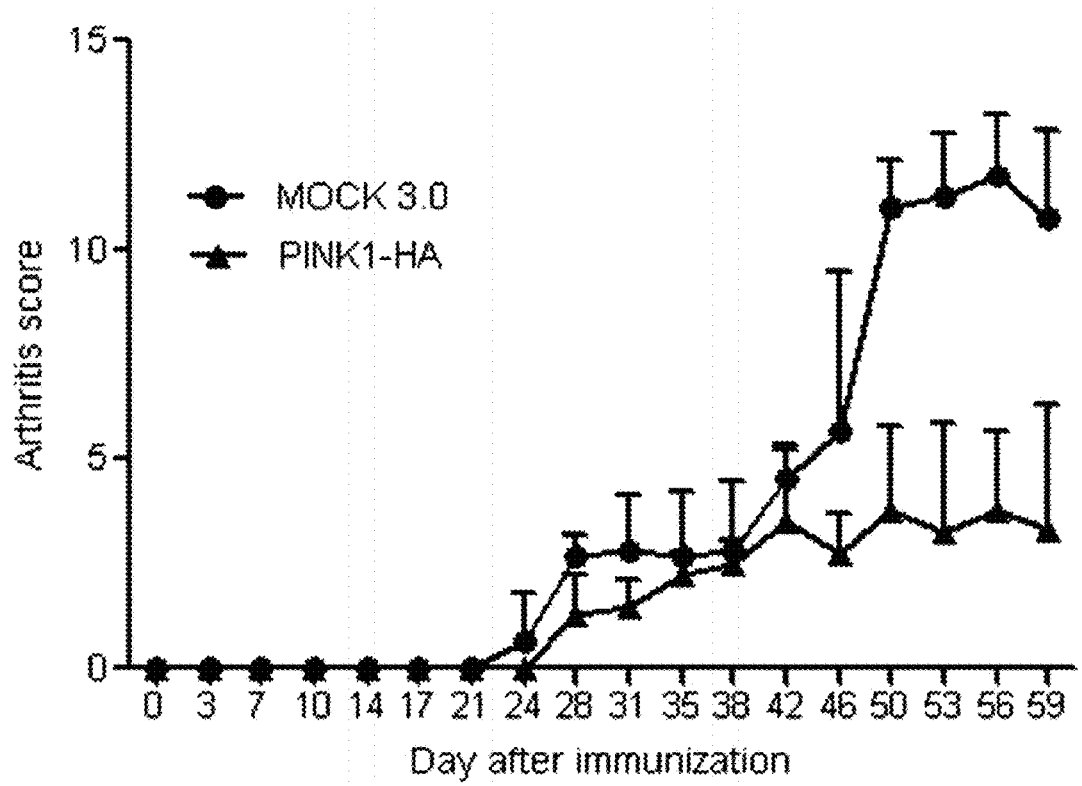
FIGS. 1A and 1B are graphs illustrating a result of verifying an arthritis index and the activity of T cells in cells separated from a lymphatic gland after injecting a PINK1 protein in an arthritis-induced animal model according to an exemplary embodiment of the present invention.
Figure 1A:
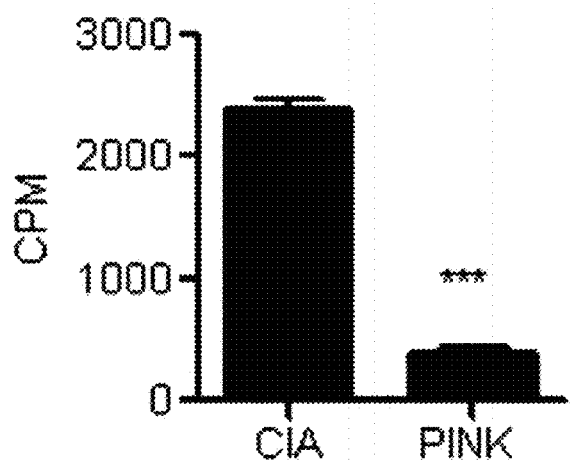

As regards the use of nucleotide symbols other than a, g, c, t, they follow the convention set forth in WIPO Standard ST.25, Appendix 2, Table 1, wherein k represents t or g; n represents a, c, t or g; m represents a or c; r represents a or g; s represents c or g; w represents a or t and y represents c or t.

```
PTEN-induced kinase 1
(Amino acids)
                                            (SEQ ID NO: 1)
Met Ala Val Arg Gln Ala Leu Gly Pro Gly Leu Gln Leu Gly Arg Ala Leu Leu Leu Arg Phe Ala Pro Lys Pro Gly Pro Leu Phe Gly Trp Gly Lys Pro Gly Pro Ala Ala Ala Trp Gly Arg Gly Glu Arg Pro Gly Gln Val Val Ser Pro Gly Ala Gln Pro Arg Pro Val Gly Leu Pro Leu Pro Asp Arg Tyr Arg Phe Arg Gln Ser Val Ala Gly Leu Ala Ala Arg Ile Gln Arg Gln Phe Met Val Arg Ala Arg Gly Gly Ala Gly Pro Cys Gly Arg Ala Val Phe Leu Ala Phe Gly Leu Gly Leu Gly Leu Ile Glu Glu Lys Gln Ala Glu Gly Arg Arg Ala Ala Ser Ala Cys Gln Glu Ile Gln Ala Ile Phe Thr Gln Lys Thr Lys Arg Val Ser Asp Pro Leu Asp Thr Arg Cys Trp Gln Gly Phe Arg Leu Glu Asp Tyr Leu Ile Gly Gln Ala Ile Gly Lys Gly Cys Asn Ala Ala Val Tyr Glu Ala Thr Met Pro Thr Leu Pro Gln His Leu Glu Lys Ala Lys His Leu Gly Leu Ile Gly Lys Gly Pro Asp Val Val Leu Lys Gly Ala Asp Gly Glu Gln Ala Pro Gly Thr Pro Thr Phe Pro Phe Ala Ile Lys Met Met Trp Asn Ile Ser Ala Gly Ser Ser Ser Glu Ala Ile Leu Ser Lys Met Ser Gln Glu Leu Val Pro Ala Ser Arg Val Ala Leu Ala Gly Glu Tyr Gly Ala Val Thr Tyr Arg Arg Ser Arg Asp Gly Pro Lys Gln Leu Ala Pro His Pro Asn Ile Ile Arg Val Phe Arg Ala Phe Thr Ser Ser Val Pro Leu Leu Pro Gly Ala Leu Ala Asp Tyr Pro Asp Met Leu Pro Pro His Tyr Tyr Pro Glu Gly Leu Gly His Gly Arg Thr Leu Phe Leu Val Met Lys Asn Tyr Pro Cys Thr Leu Arg Gln Tyr Leu Glu Glu Gln Thr Pro Ser Ser Arg Leu Ala Thr Met Met Thr Leu Gln Leu Leu Glu Gly Val Asp His Leu Val Gln Gln Gly Ile Ala His Arg Asp Leu Lys Ser Asp Asn Ile Leu Val Glu Trp Asp Ser Asp Gly Cys Pro Trp Leu Val Ile Ser Asp Phe Gly Cys Cys Leu Ala Asp Gln His Val Gly Leu Arg Leu Pro Phe Asn Ser Ser Ser Val Glu Arg Gly Gly Asn Gly Ser Leu Met Ala Pro Glu Val Ser Thr Ala His Ser Gly Pro Ser Ala Val Ile Asp Tyr Ser Lys Ala Asp Thr Trp Ala Val Gly Ala Ile Ala Tyr Glu Ile Phe Gly Leu Ala Asn Pro Phe Tyr Gly Gln Gly Ser Ala His Leu Glu Ser Arg Ser Tyr Gln Glu Ala Gln Leu Pro Glu Met Pro Glu Ser Val Pro Pro Glu Ala Arg Arg Leu Val Arg Ser Leu Leu Gln Arg Glu Ala Ser Lys Arg Pro Ser Ala Arg Leu Ala Ala Asn Val Leu His Leu Ser Leu Trp Gly Glu His Leu Leu Ala Leu Lys Asn Leu Lys Leu Asp Lys Met Ile Ala Trp Leu Leu Gln Gln Ser Ala Ala Thr Leu Leu Ala Asp Arg Leu Arg Glu Lys Ser Cys Val Glu Thr Lys Leu Gln Met Leu Phe Leu Ala Asn Leu Glu Cys Glu Ala Leu Cys Gln Ala Ala Leu Leu Leu Ser Ser Trp Arg Ala Ala Pro PTEN-induced kinase 1
(DNA)
                                            (SEQ ID NO: 2)
atggcggtgc gacaggcact gggcccaggc ctgcagctgg gtcgggcgct gctgctgcgc ttcgcgccca agcccggccc gctgttcggc tgggggaagc ccggccccgc ggcggcctgg ggccgcggag agcgcccagg ccaggtcgta agccccggag cacagcctcg gccggtcggg ctccccctcc
```

-continued

```
cggaccgcta ccgcttcttc cgccagtcgg tagctgggct ggcggcgcggatccagaggc agttcatggt gcgggcccgg ggcggcgcag gcccttgcgg ccgagcggtcttcctggcct tcgggctggg gctggggctg atcgaggaga agcaggcgga aggccggagggccgcctcgg cctgtcagga gatccaggca atttttacac agaaaaccaa gcgcgtgtctgacccactgg acactcgatg ctggcagggc ttccgtctgg aggattatct gatagggcaagccattggca agggttgcaa tgccgctgtg tatgaagcca ccatgcccac gctgccccagcacctggaaa aggccaaaca ccttggcctt ataggaaagg gcccggatgt cgtcctgaagggagcagacg gggagcaggc tccagggact cccacctttc cctttgccat caagatgatgtggaatatct cggcaggttc ctccagcgaa gccatcttaa gcaaaatgag ccaggagctggtcccggcaa gccgcgtggc tttggctgga gagtatggag cagttactta cagaagatccagagatggtc ccaagcagct tgccccacac cctaacatca tccgggtttt ccgcgccttcacctcatctg tgccctcct gccggggcc ctggctgact atcctgatat cctaccccacactactacc caaaagacct aagccacgat cacacactgt tcctcattat gaagaactacccctgtaccc tgcgccagta ccttgaggag cagactccca gttctcgcct ggctaccatgatgaccttgc agttgctgga gggcgtggac catctggttc agcagggcat tgcccatcgggatctcaagt ccgacaacat ccttgtggag tgggactcag atggctgtcc ctggctagtgatctcagact ttggctgctg cctggctgac cagcatgttg gcctgcggct gcctttcaacagctccagtg tagagcgtgg tggcaatggc tccctgatgg cccctgaggt gtccacagcccattctggcc ccagtgcggt aattgactac agcaaagccg atacctgggc tgtgggggccatcgcctatg aaatctttgg gcttgccaat cccttctatg gccaaggcag tgcccacctcgagagccgca gctaccagga agctcagctg cctgagatgc ctgagtcggt gcctccagaggcaagacggc tggtgaggtc actgctccag cgagaggcca gcaagagacc gtctgcacgcttagctgcaa atgtgctgca cttaagcctc tggggcgagc atcttctagc cctgaagaacctgaaattgg acaagatgat cgcctggctc ttgcagcagt cagcagccac tctgctggctgacaggctga gagagaagag ctgcgtggag acaaagctgc agatgctgtt tctggctaacctggagtgtg aggctctctg ccaggcagcc ctcctcctct cttcctggag ggcagccccat
```

MODES OF THE INVENTION

Hereinafter, exemplary embodiments of the present invention will be described in detail. However, the present invention is not limited to the exemplary embodiments disclosed below, but can be implemented in various forms. The following exemplary embodiments are described in order to enable those of ordinary skill in the art to embody and practice the invention.

Example 1

Measurement of Arthritis Improvement Degree and Analysis of Activity Degree of T Cell According to PINK1 Protein Treatment In order to check whether the PINK1 protein has an effect on prevention and treatment of arthritis, the inventors first prepared an arthritis model by injecting type II collagen into a DBA1/J normal mouse and measured an arthritis index after injecting a PINK1 DNA vector to the animal model.

To this end, the inventors performed primary immune by mixing 100 μg of type II collagen and a complete Freund's adjuvant (CFA) and injecting the mixture to a subcutaneous tail of the mouse to perform primary immune and performed booster immune by mixing 100 μg of type II collagen and an incomplete Freund's adjuvant (IFA) and re-injecting the mixture to the subcutaneous tail after 2 weeks of the primary immune. The PINK DNA vector of 100 μg was injected through the vein after one week after injecting the type II collagen and injected to the right and left rear leg muscles of the mouse at an interval of 1 week after the vein injection. PINK1 was expanded from human cDNA and cut with Hind III and EcoR1 to be inserted to pcDNA3.1 (Invitrogen) and it was verified that the expression of the inserted PINK1 was over-expression with a western blot by using a protein lysate obtained by transduction to COS cells. A group using a mock vector instead of the PINK vector was set a control group.

Further, in order to analyze the effect of PINK 1 protein on a T cell activity, the inventors evaluated the cell proliferation activity degree by separating T cells from the splenocyte of the arthritis model mouse, anti-CD3 stimulating the separated T cells for three days to activate the T cells, and processing the activated T cells with 3H isotopes.

Further, the expression degree of IgG and IgG1 was examined by using a sandwich ELISA in the serum of each mouse group. To this end, monoclonal anti-mouse IgG reacted for 1 hour at room temperature on a 96-well plate and treated with a blocking solution (1% BSA/PBST) to block a non-specific bind. The serum of the mouse control group was continuously diluted by ½ to be used as a standard and reacted for 1 hour at room temperature by adding a cell culture supernatant. Thereafter, anti-mouse IgG-HRP reacted for 1 hour at room temperature and washed four times after reaction, and then colored through a TMB system, and absorbance was measured at a wavelength of 450 nm.

Figure 1B:
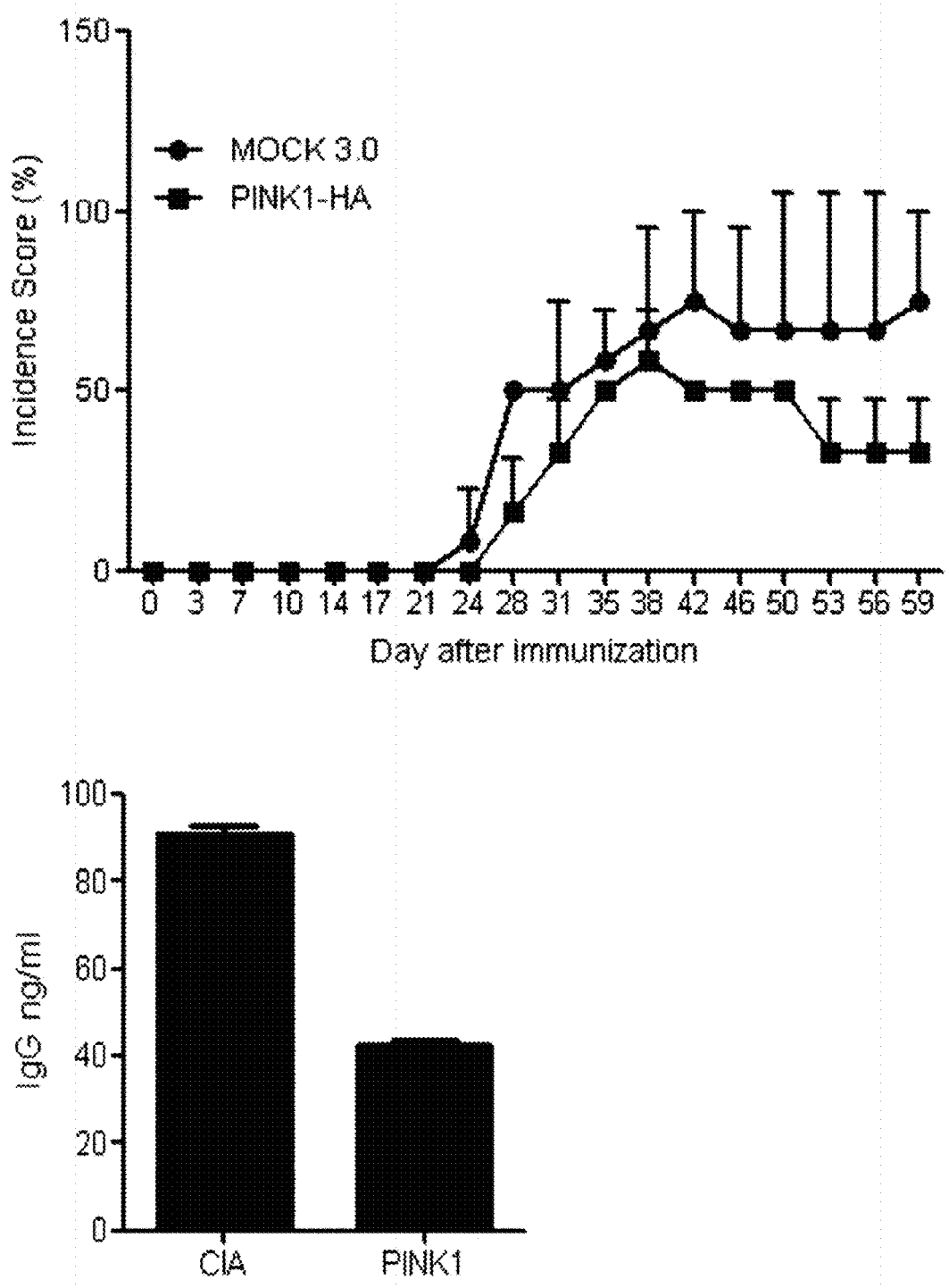

As a result, as compared with a control group which is not treated with the PINK1 protein, in an experimental group administrated with the PINK1 protein of the present invention, the arthritis index was decreased almost 70%. Further, in the PINK1 injection group, it could be seen that the CPM which is the proliferation index in the T cells was decreased and thus the proliferation activity of the T cells was significantly inhibited when administrating the PINK1 protein (see FIG. 1A). Further, as compared with the control group which is not treated with the PINK1 protein, in an experimental group administrated with the PINK1 protein of the present invention, the disease severity index was significantly decreased and the expression amount of IgG in the serum which was the activity index of arthritis disease was significantly suppressed (see FIG. 1B).

Example 2

Analysis of Effect on the Articular Destruction Degree of Articular Tissue of PINK1 Protein The inventors conducted histological examination for the articular tissue in the arthritis mouse animal model in order to analyze the arthritis improvement degree according to the PINK1 protein treatment.

To this end, in the animal and the control group which were administrated with the PINK1 protein, the rear leg of each mouse group at 56 days after arthritis induction was fixed with 10% formalin and a calcareous compound was removed from the bone, and then a block was prepared with paraffin. From this, an articular piece (7 μm) was prepared and attached on a slide, and subjected to a deparaffin process by using xylene, wetted by using ethanol with high-concentration and low-concentration, and stained with haematoxylin and eosin. Further, in order to verify the cartilage destruction degree, the articular piece was stained with toluidine blue and safranine O.

Figure 2A:
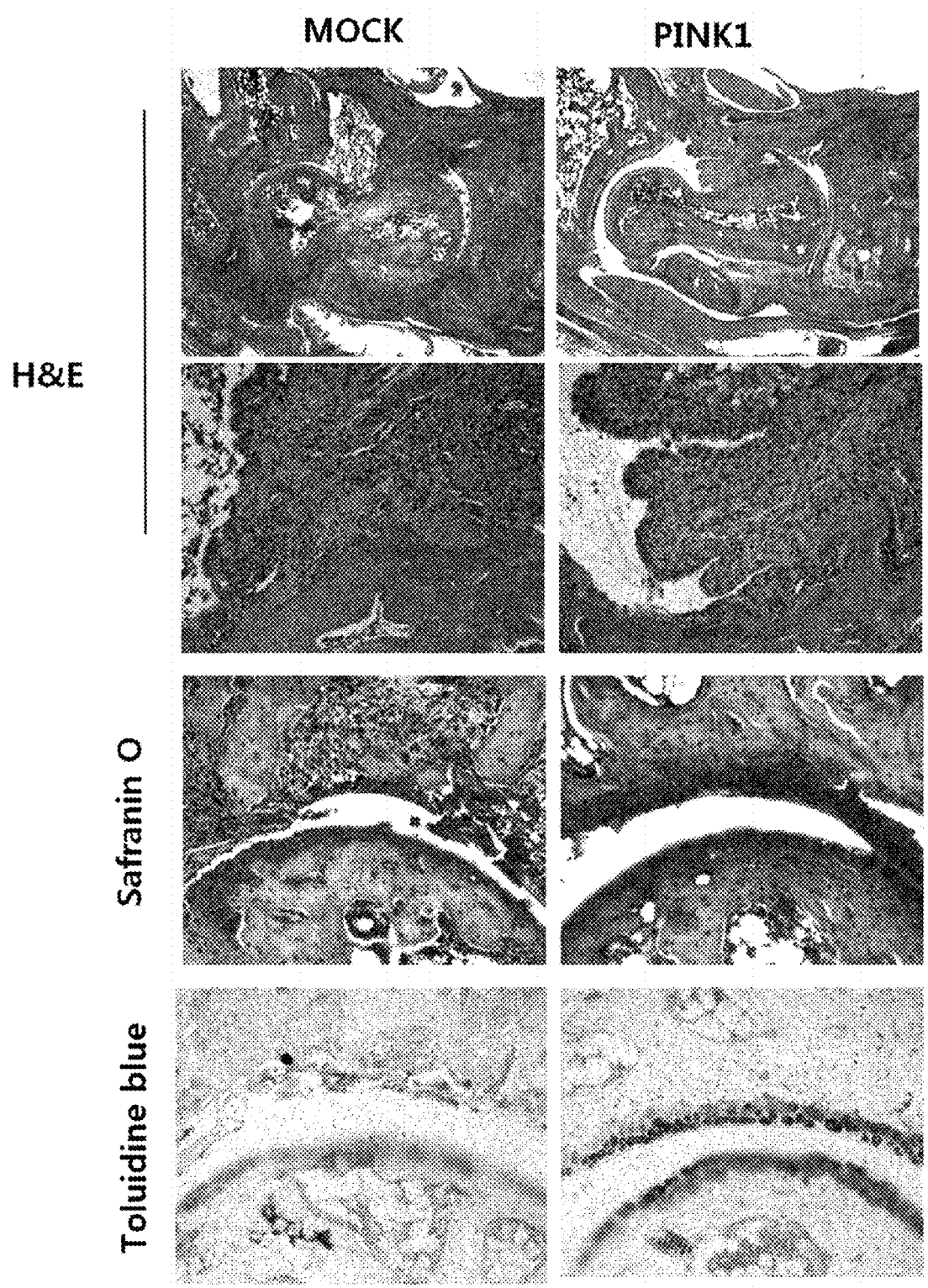
FIGS. 2A and 2B are results of verifying cartilage destruction and infiltration of inflammatory cells through hematoxylin eosin staining and toluidine blue and safranin O staining in a group treated with PINK1 protein and a group not treated with the PINK1 protein as a control group in an arthritis induced animal model according to an exemplary embodiment of the present invention.
Figure 2B:
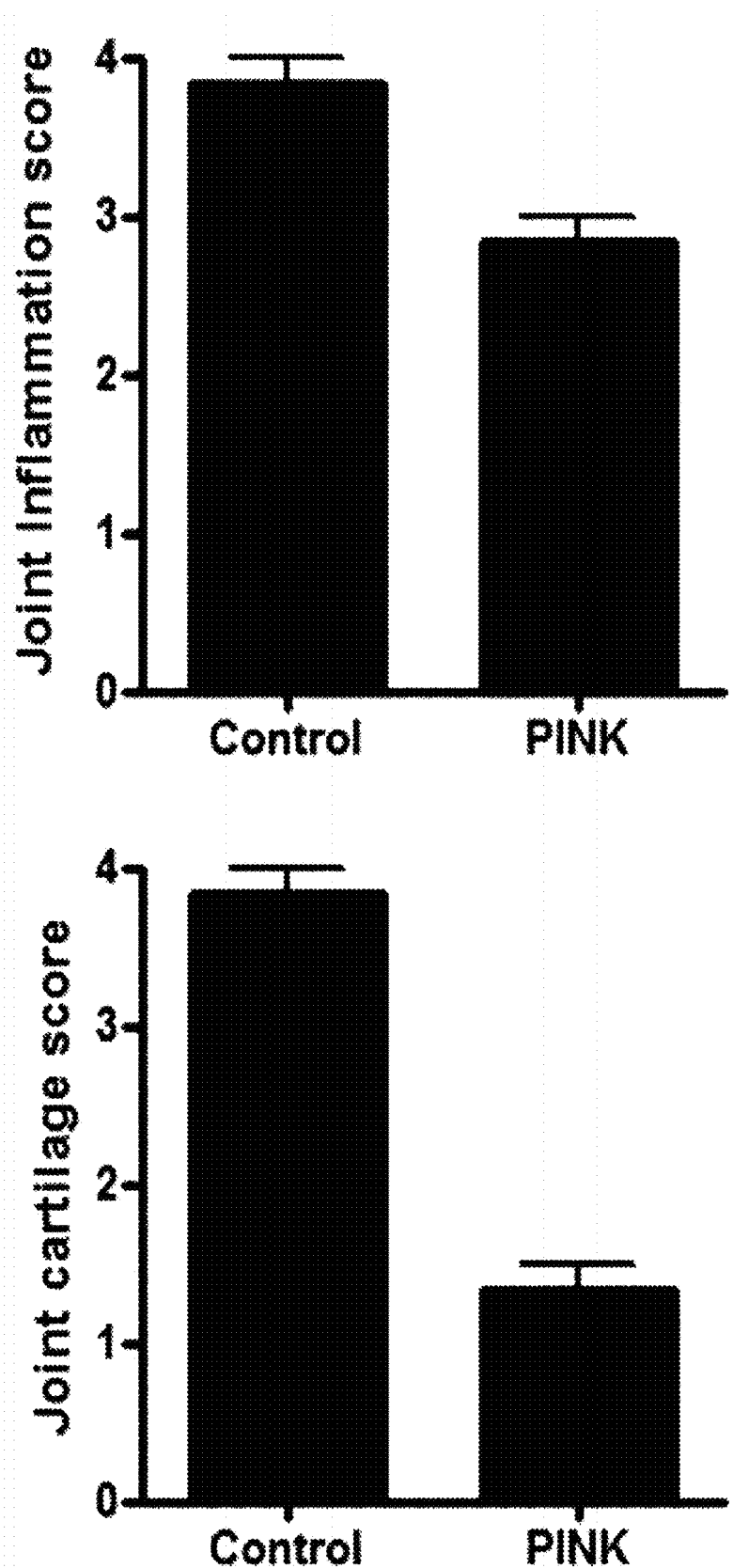

As a result of observing cartilage and inflammation in the joint of the experimental animal group after the above experiment, the joint of the control group which was not treated with the PINK1 protein was broken and inflammatory cells were infiltrated. However, in the experimental animal group which was injected with the PINK1 protein of the present invention, as compared with the control group, it was verified that the osteophage differentiation was decreased and the infiltration of the inflammatory cells was suppressed (see FIGS. 2A and 2B).

Example 3

Effect of Inhibiting Expression of Inflammatory Cytokine in Articular Tissue by PINK1 Protein Treatment in Arthritis Animal Model The inventors additionally conducted histological examination for the articular tissue in the arthritis mouse animal model in order to analyze the expression of inflammatory cytokine in the articular tissue according to the PINK1 protein treatment.

To this end, the inventor prepared an articular piece (7 μm) in the same manner as Example 2, attached the articular piece on a slide, stained IL-17, IL-6, IL-1b, and TNF-α which were representative inflammatory cytokines associated with autoimmune arthritis by using an immunochemistry staining method, and analyzed the stained articular piece through an optical microscope.

Figure 3:
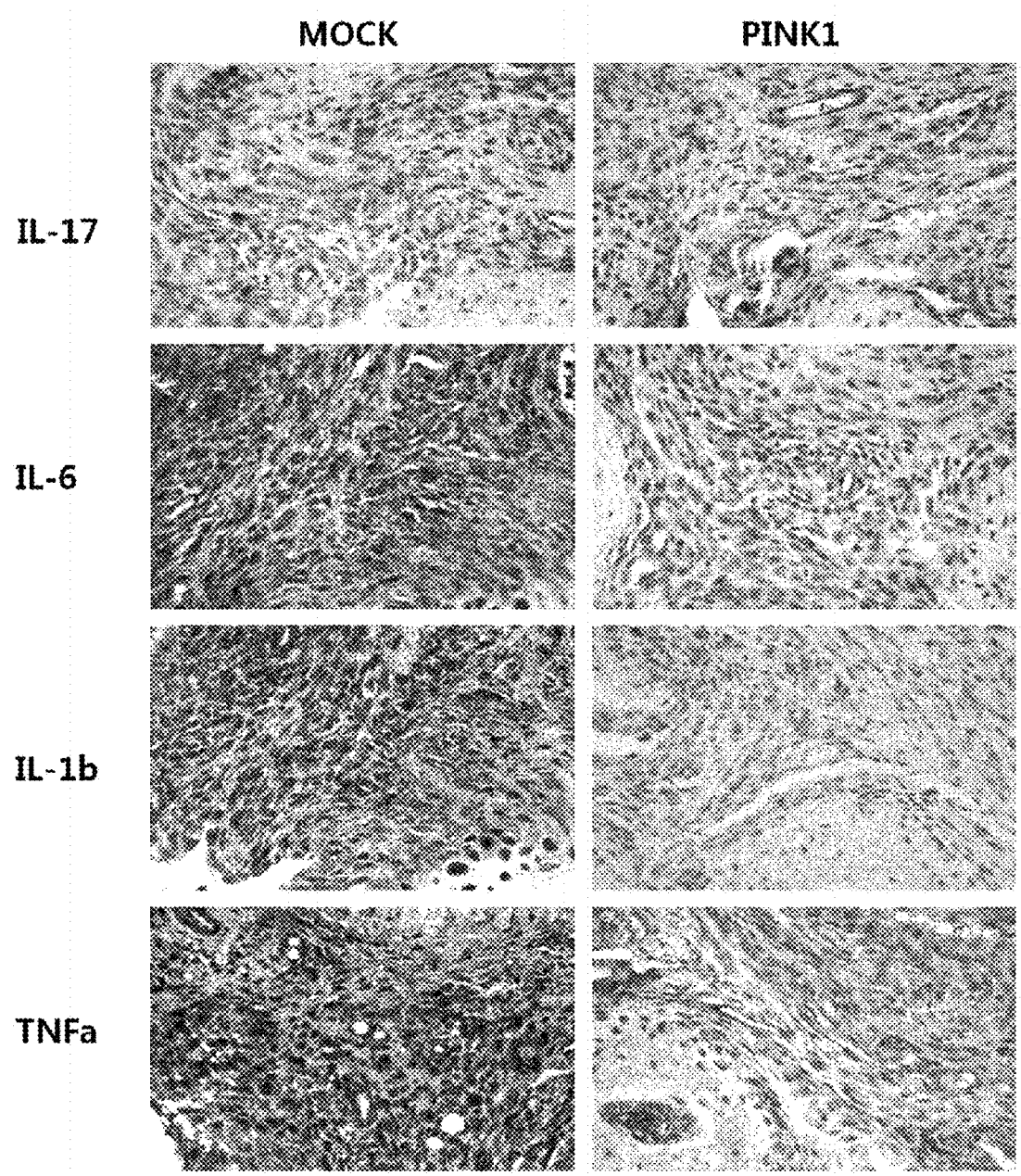
FIG. 3 is an immunohistochemical staining photograph showing inhibition of expression of inflammatory cytokines in an articular tissue by the PINK1 protein in the arthritis induced animal model according to the exemplary embodiment of the present invention.

As a result, in the articular tissue of the PINK1 protein injection group of the present invention, the expression of IL-17, IL-6, IL-1b, and TNF-α was significantly inhibited as compared with the control group, and from the result, it was verified that the PINK1 protein may control the activity of the inflammatory cytokine in the autoimmune arthritis disease (see FIG. 3).

Example 4

Effect of Simultaneously Controlling Th17 and Treg Cells by PINK1 Protein Treatment in Arthritis Animal Model The inventors conducted a parenchyma cell analysis in the splenocyte of the arthritis mouse animal model in order to verify an effect of simultaneously controlling Th17 and Treg cells according to the PINK1 protein treatment.

To this end, the inventors reacted anti-CD4-PerCP and anti-CD25-APC at 4° C. for 30 minutes in the splenocyte of each mouse, permeabilized the cells after reaction, and then reacted permeabilized cells with anti-IL-17-PE, anti-IFNr-FITC, or anti-Foxp3-PE fluorescent antibody. After the reaction, each cell was analyzed by using a FACS caliber.

Figure 4A:
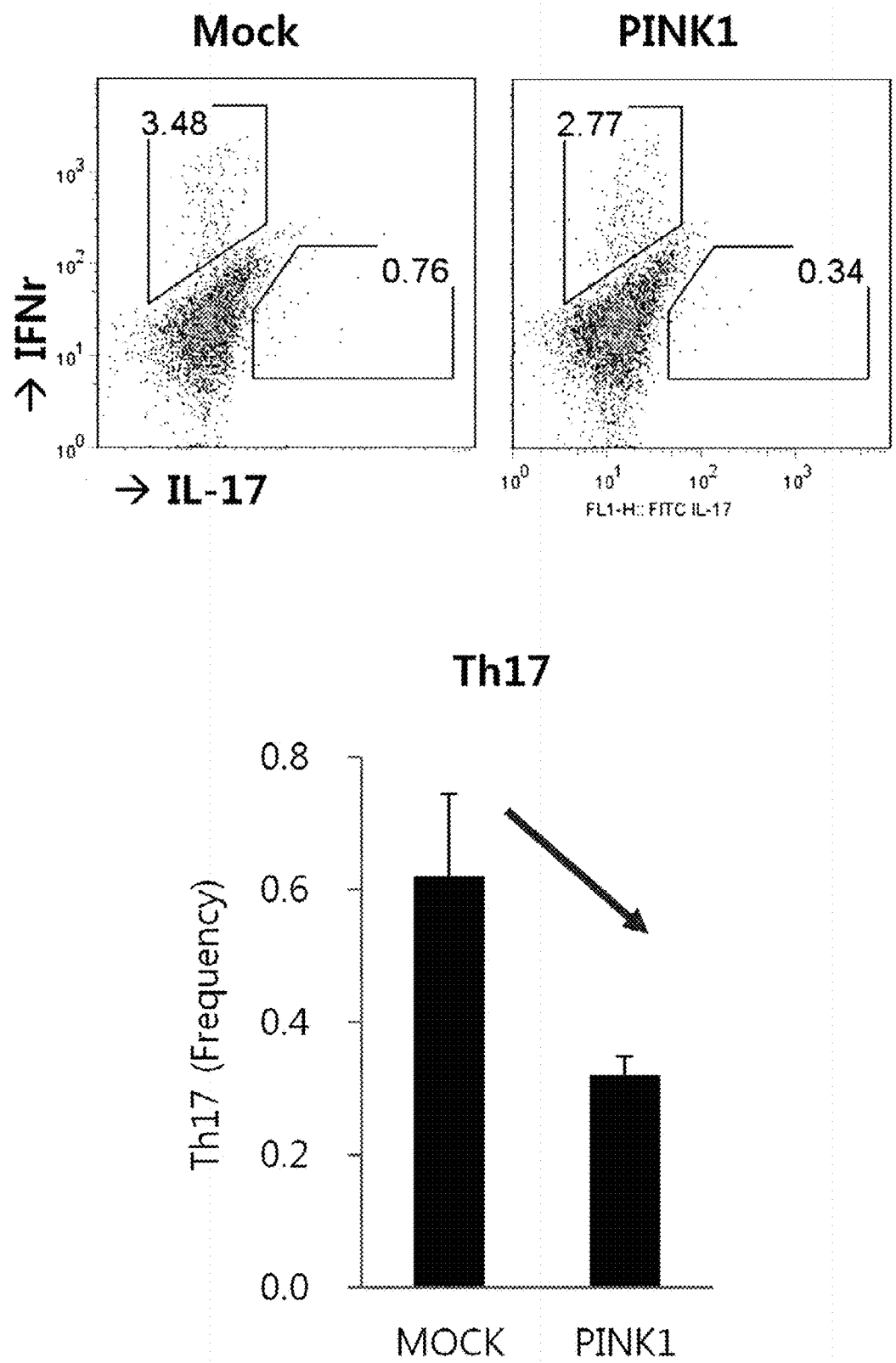
FIGS. 4A and 4B are a result and a graph of parenchyma cell analysis showing an effect of simultaneously controlling Th17 and Treg cells by the PINK1 protein treatment in the arthritis induced animal model according to the exemplary embodiment of the present invention.
Figure 4B:
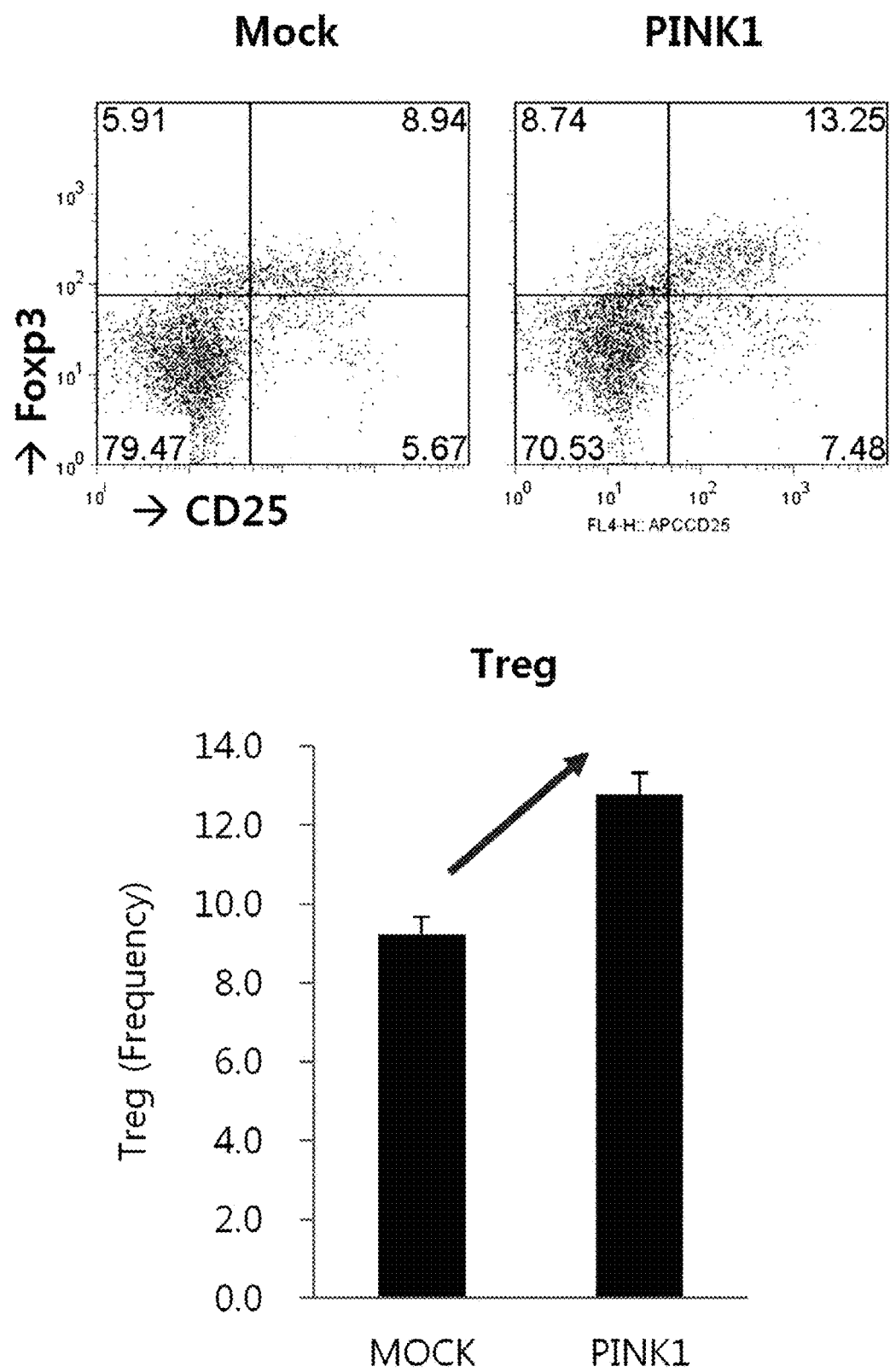

As a result, in the group injected with the PINK1 protein, it was shown that the Th17 cells were decreased by more than half (see FIG. 4A) and the Treg cells were increased almost two times (see FIG. 4B), and from the result, the PINK1 protein may control simultaneously the activity of Th17/Treg cells.

Example 5

Effect of Inhibiting Th17 Cells by PINK1 Protein Treatment in Arthritis Animal Model The inventors verified the expression amount of Th17 cells by using a confocal microscope after staining anti-CD4-pe and anti-IL-17-FITC or staining anti-CD4-pe and anti-pSTAT3 705-FITC in cells ($1\times10^6$) separate from the spleen of the mouse in order to examine whether the PINK1 protein treatment of the present invention had any effect on the Th17 cells. Further, after processing RNA zolB in the splenocyte of each mouse to isolate RNA, expression of RORrT genes was analyzed by a realtime PCR by synthesizing cDNA from the isolated RNA.

Figure 5A:
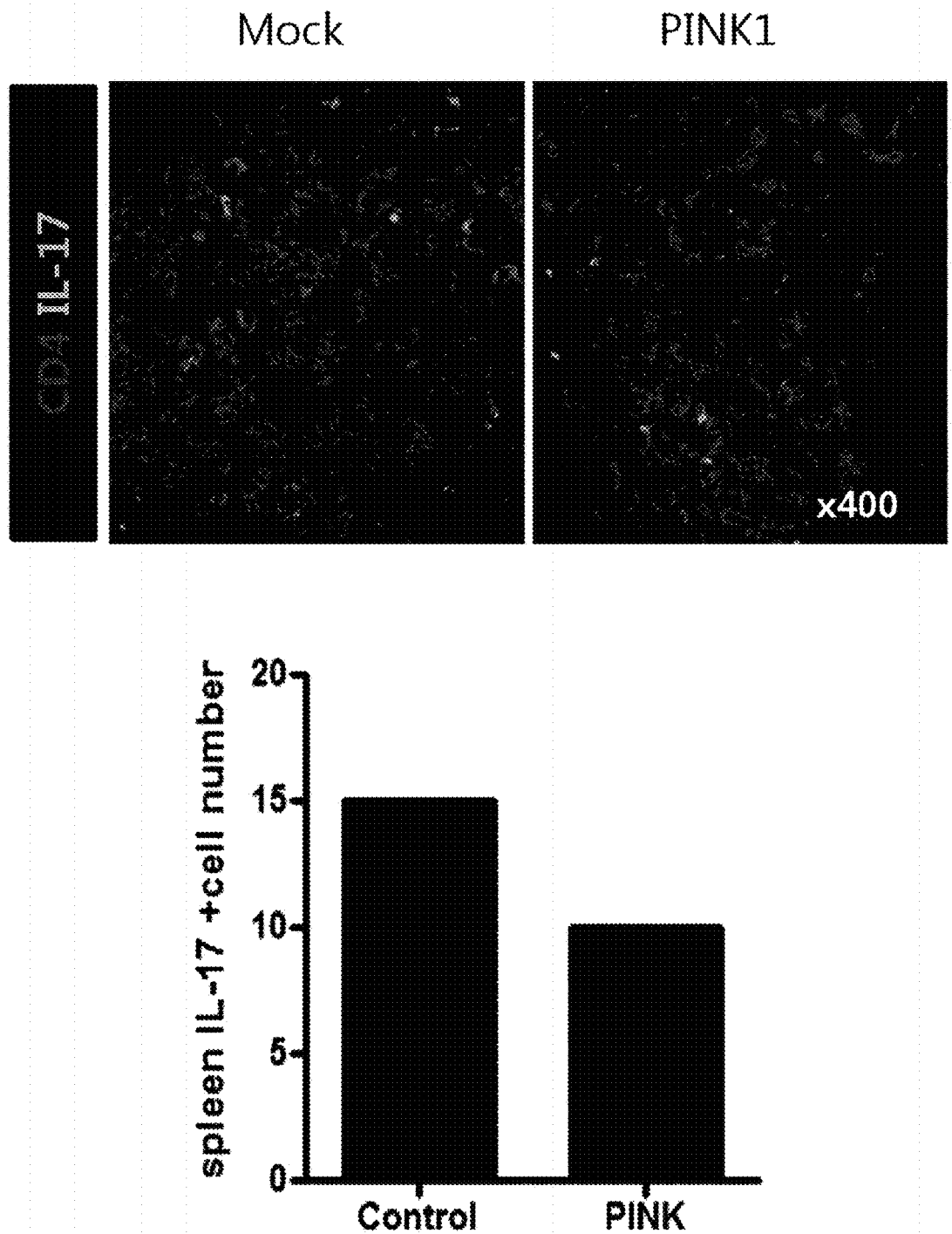
FIGS. 5A to 5C are a photograph of verifying cells expressing IL-17 and STAT3 genes through a confocal microscope and a graph showing expression of a RORrT gene which is a transcription factor of a Th17 cell in the splenocytes of when treating the PINK1 protein and the non-treated group as the control group in the arthritis induced animal model according to the exemplary embodiment of the present invention.
Figure 5B:
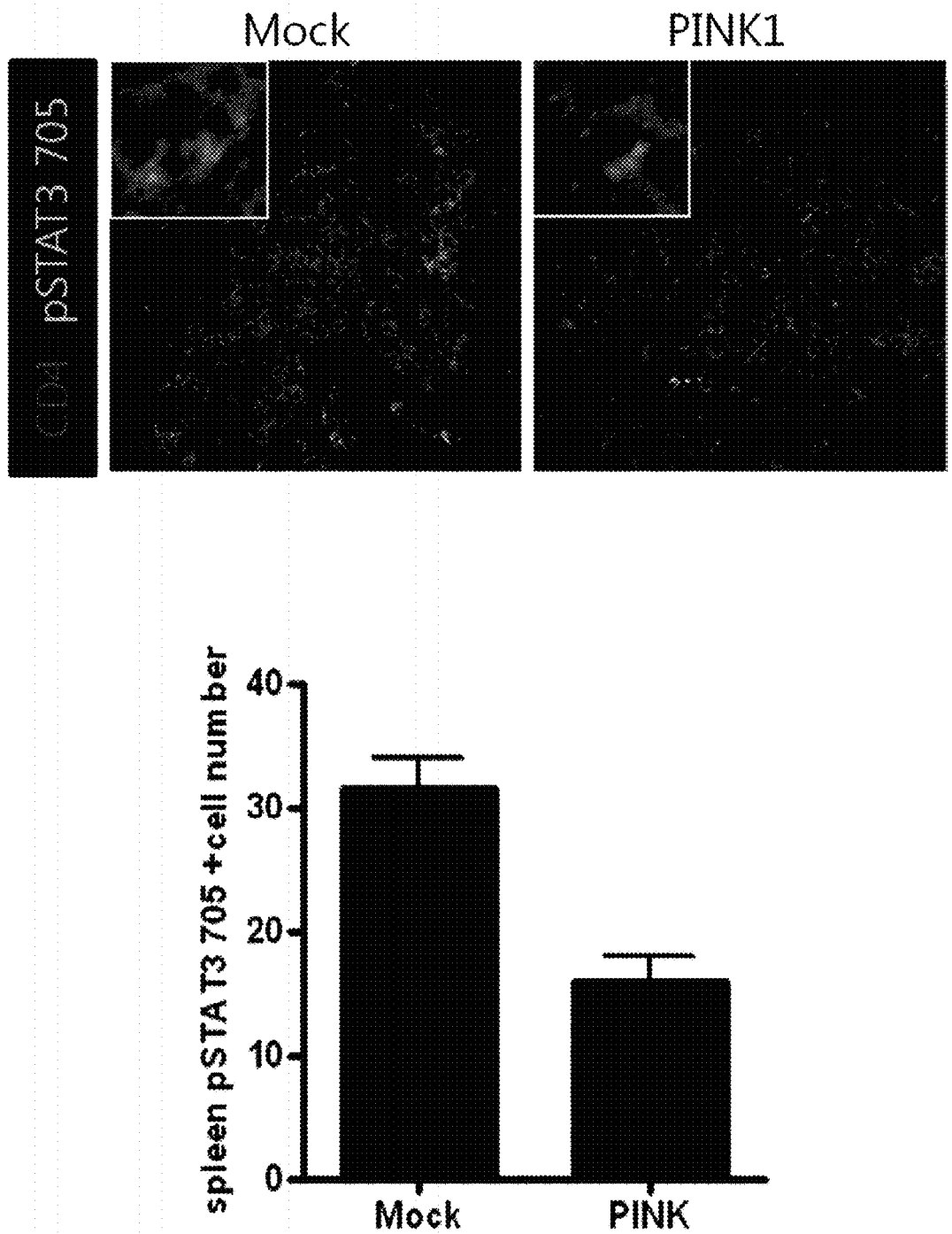
Figure 5C:
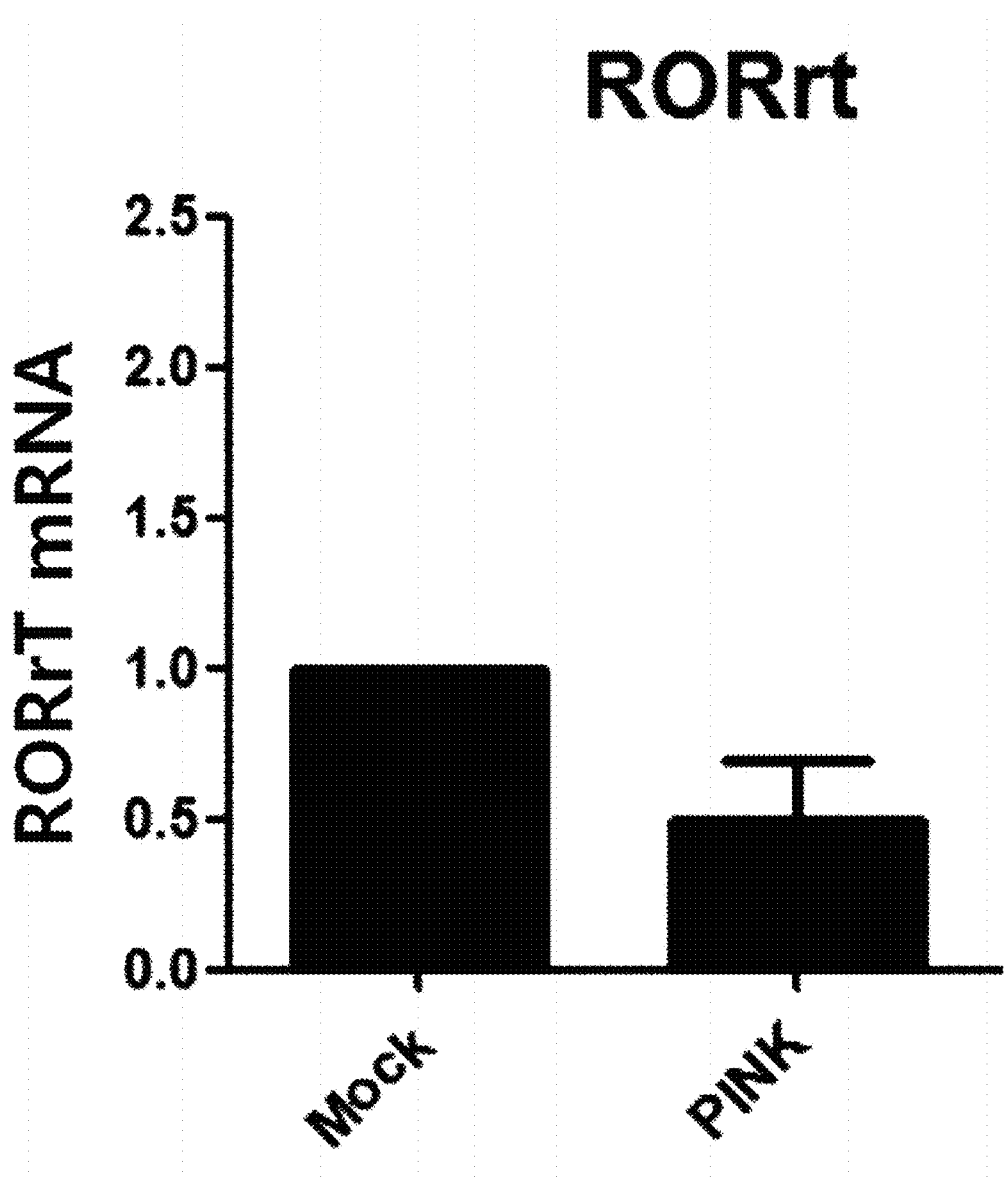

As a result, as compared with the arthritis experimental animal as the control group, the Th17 cells as pathologic cells were significantly inhibited in the spleen of the mouse treated with the PINK1 protein (see FIG. 5A) and the expression of the RORrT gene which was the transcription factor of the Th17 cells was inhibited (see FIG. 5C). Further, as a result of verifying the activity of STAT3 which was the transcription factor of the Th17 cells in the spleen tissue, the expression of phosphorylated STAT3 was significantly inhibited in the PINK1 injection group (see FIG. 5B). From the result, it was verified that PINK may control the activity of RORrT and STAT3 when suppressive-controlling the activity of Th17 cells.

Example 6

Effect of Increasing Treg Cells by PINK1 Protein Treatment in Arthritis Animal Model The inventors verified the expression amount of Treg cells by using a confocal microscope after staining anti-CD4-pe, anti-CD25-APC, and anti-Foxp3-FITC or staining anti-CD4-pe and anti-pSTAT3 705-FITC in cells ($1\times10^6$) separate from the spleen of the mouse in order to examine whether the PINK1 protein treatment of the present invention had any effect on the Treg cells. Further, after processing RNA zolB in the splenocyte of each mouse to isolate RNA, the expression of Foxp3 and SOCS3 genes was analyzed by a realtime PCR by synthesizing cDNA from the isolated RNA.

Figure 6A:
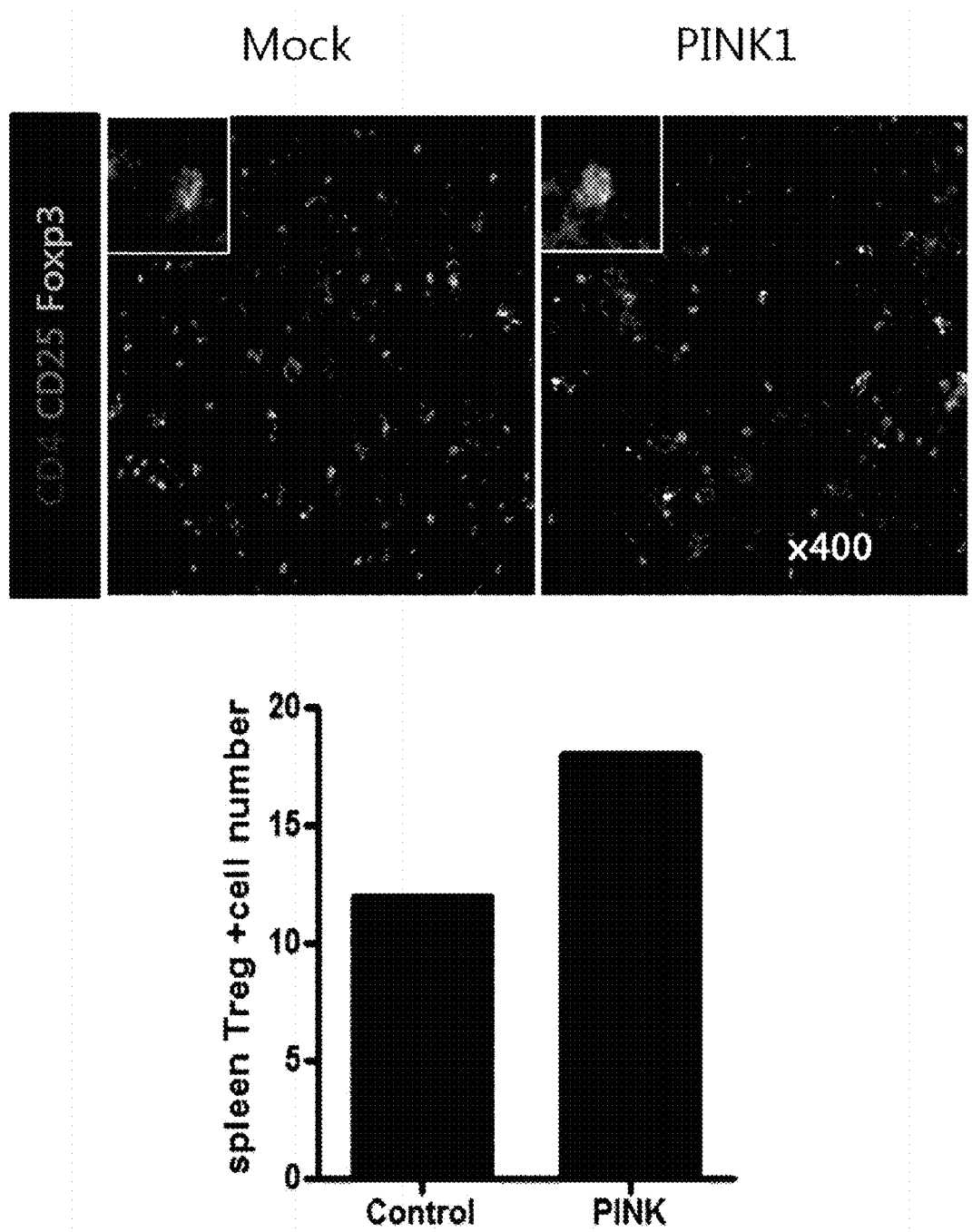
FIGS. 6A to 6C are a photograph of verifying cells expressing CD25 and STAT5 genes through a confocal microscope and a graph showing expression of a STAT5 gene which is a transcription factor of a Treg cell in the splenocytes of when treating the PINK1 protein and the non-treated group as the control group in the arthritis induced animal model according to the exemplary embodiment of the present invention.
Figure 6B:
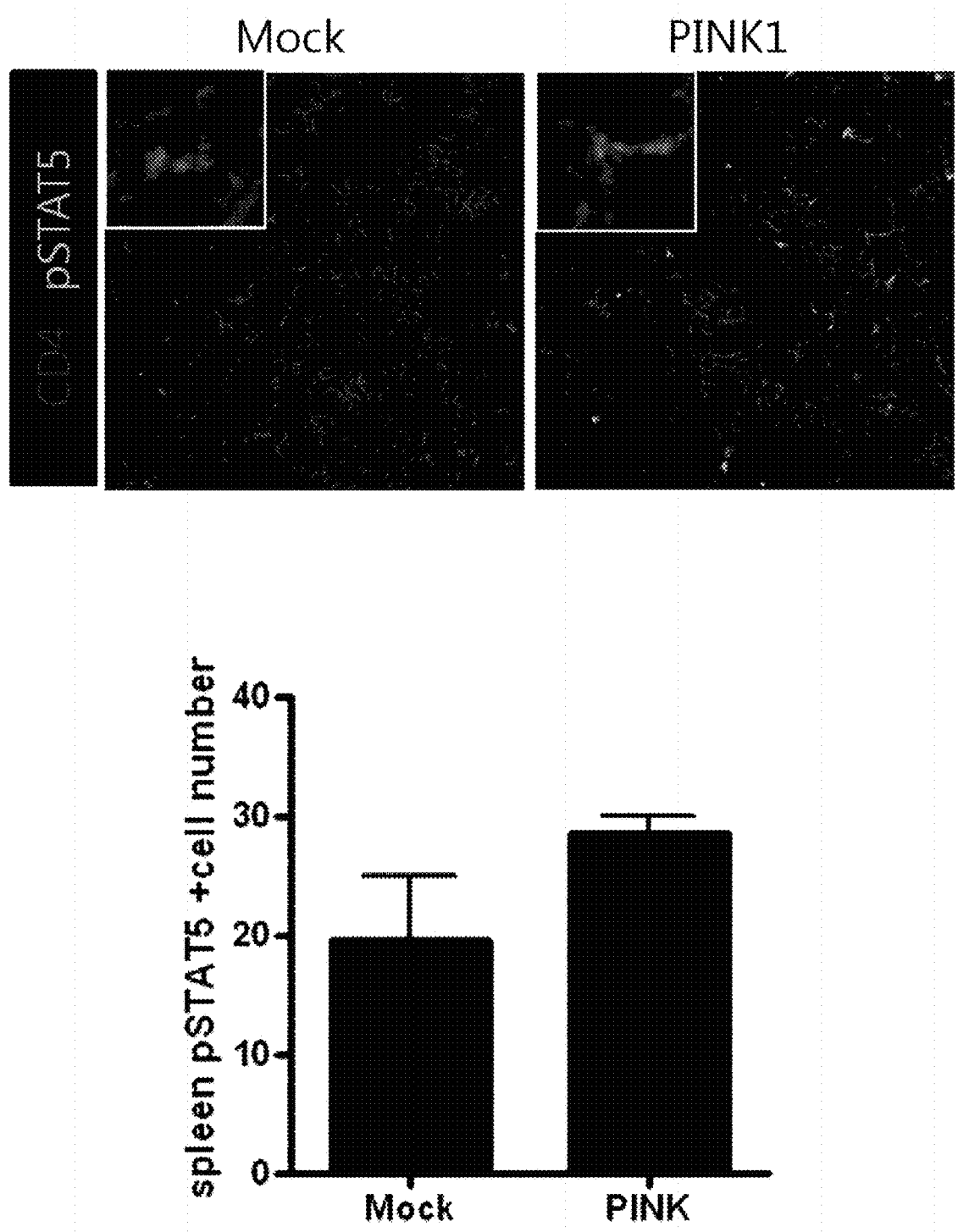
Figure 6C:
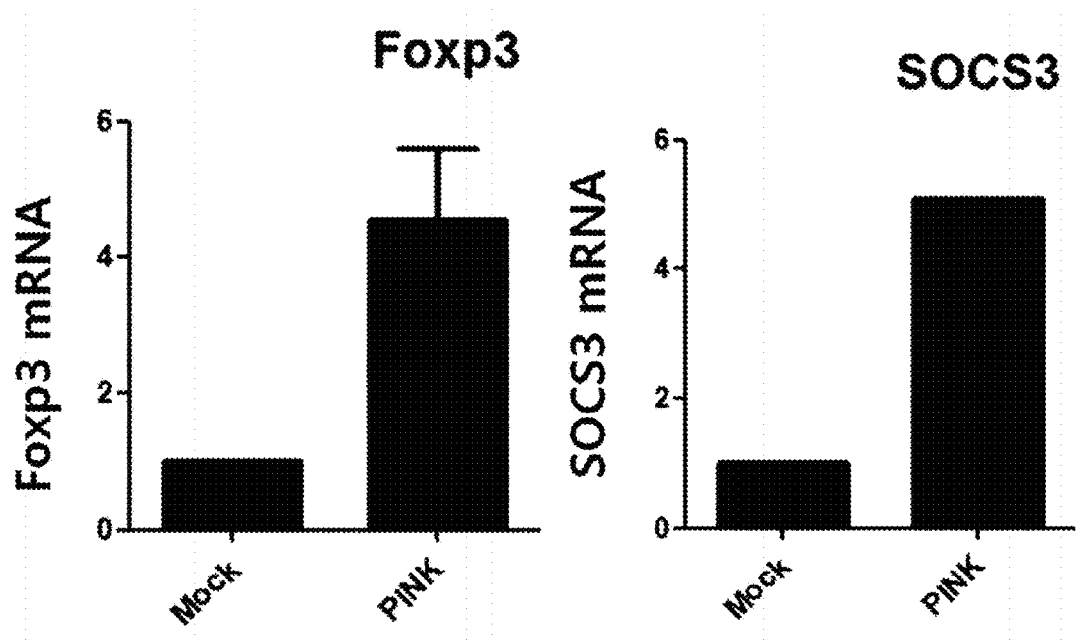

As a result, as compared with the arthritis experimental animal as the control group, the expression of Treg cells was significantly increased in the spleen of the mouse treated with the PINK1 protein (see FIG. 6A) and as result of verifying the expression of STAT5 which was the transcription factor of the Treg cells in the spleen tissue, the expression of phosphorylated STAT5 was significantly increased in the PINK1 injection group (see FIG. 6B). Further, the expression of Foxp3 and SOCS3 genes which were representative transcription factors of the Treg cells was increased (see FIG. 6C).

Example 7

Effect of Suppressive-Controlling Inflammatory Cytokine by In Vitro Transfection of PINK1 Gene The inventors activated cells to conA after injecting each vector into NIH T cells. The expression degree of TNF-α was examined by using a sandwich ELISA by collecting a cultured supernatant after 3 days of injection each vector. To this end, a monoclonal anti-TNF-α antibody of 2 µg/ml was reacted on a 96-well plate at 4° C. all night and a non-specific bond was blocked with a blocked solution (1% BSA/PBST) after reaction. A TNF-α recombinant was continuously diluted by ½ concentration to be used as a standard and reacted at room temperature for 2 hours by adding a cell-culture supernatant. Thereafter, a biotinylated anti-TNF-α antibody was reacted at room temperature for 2 hours and washed four times after reaction and reacted at room temperature for 2 hours after diluting and adding an extraavidin-alkaline phosphatase conjugate. After reaction, a PNPP/DEA was added and colored, and absorbance was measured at a wavelength of 405 nm after coloring.

Figure 7:
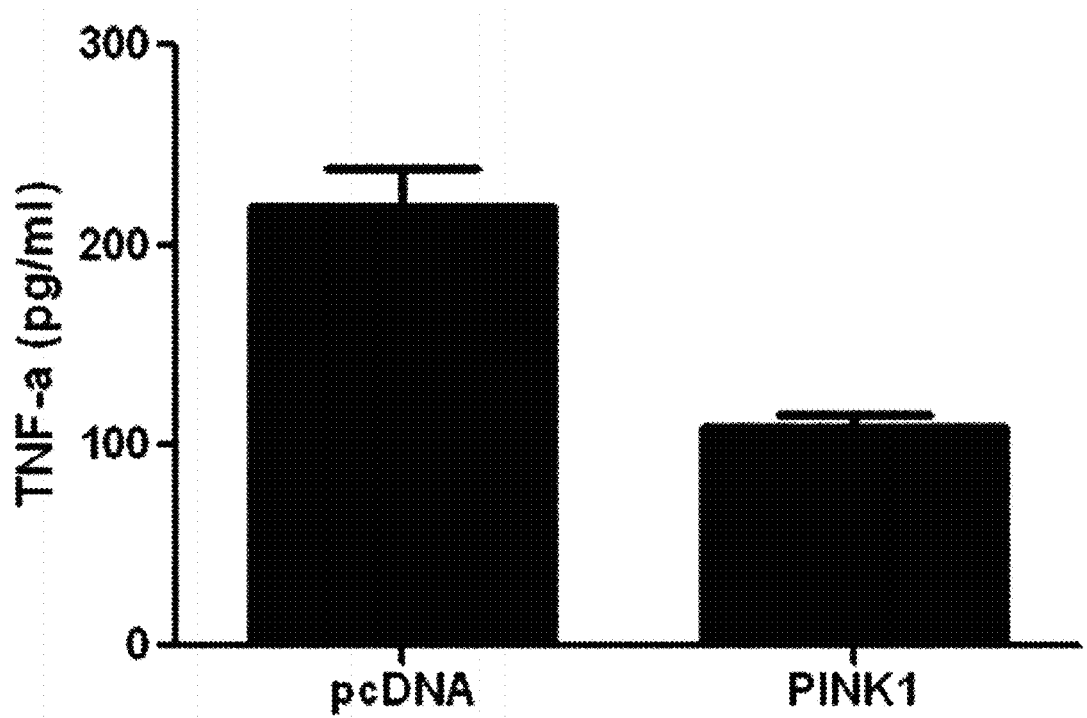
FIG. 7 is a graph showing an effect of suppressive-controlling inflammatory cytokines due to in vitro transfection of a PINK1 gene in a NIH T cell according to the exemplary embodiment of the present invention.

As a result, in the cells injected with the PINK1 gene, the expression of TNF-α according to conA reaction was significantly inhibited (see FIG. 7). From the result, even in an efficacy evaluation in vitro, the PINK1 protein may directly control the expression of inflammatory cytokines.

Example 8

Analysis of Activity of Autophagy by PINK1 Protein Treatment in Arthritis Animal Model The inventors verified whether the PINK1 protein activated the autophagy and whether the Th17 cells were decreased and actually, the Treg cells were increased by the mechanism in order to more clearly understand a mechanism associated with reduction of the Th17 cells and an increase of the Treg cells which were observed in Examples 5 and 6. To this end, the inventors performed a confocal microscopy analysis after staining the splenocytes of the mouse with anti-CD4-percp, anti-CD25-APC, anti-Foxp3-PE and anti-LC3-FITC or anti-CD4-percp, anti-CD25-APC, anti-Foxp3-PE and anti-coxiV-FITC.

Figure 8A:
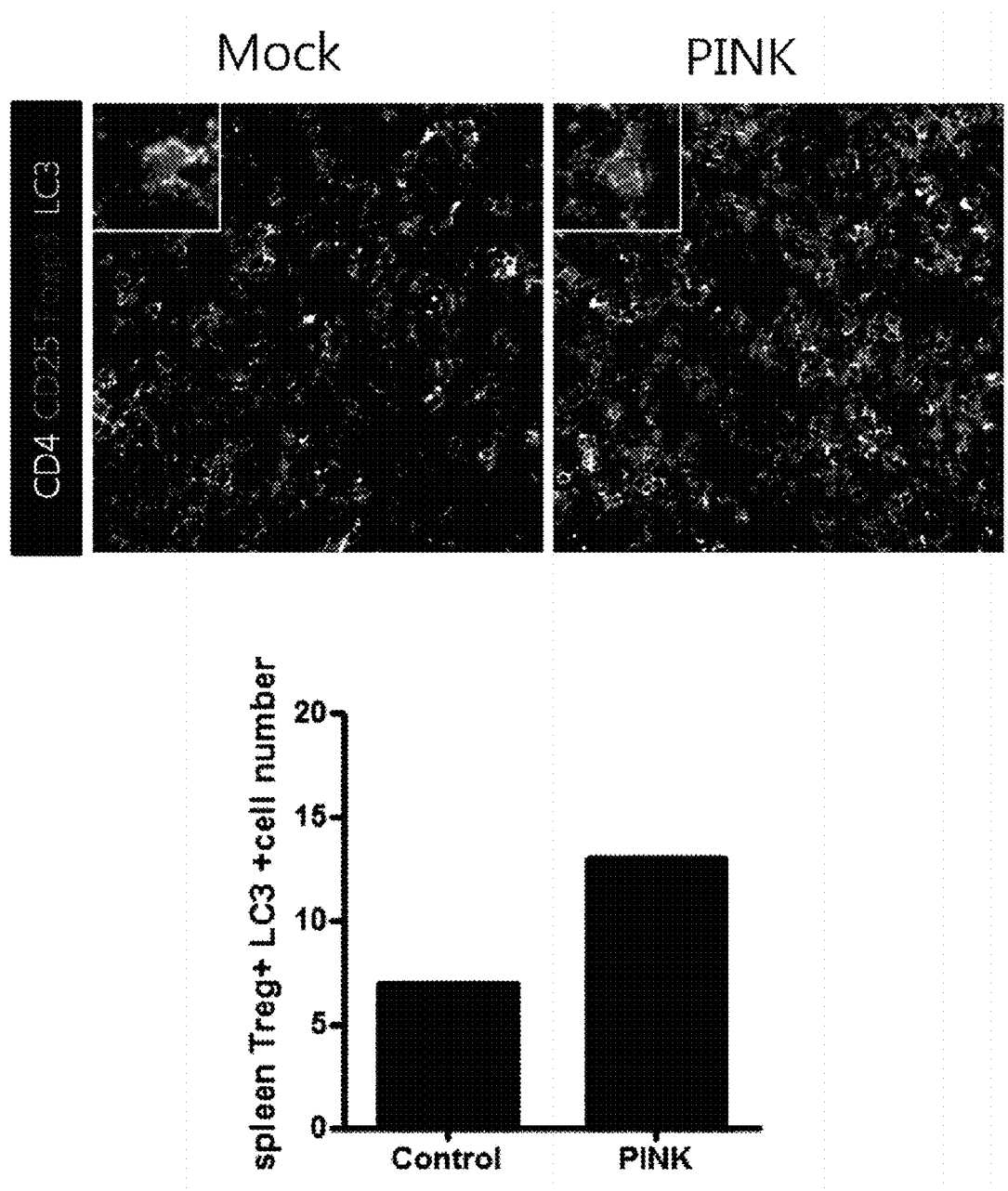
FIGS. 8A and 8B are a photograph and a graph showing a result of verifying autophagy expressed in Th17 and Treg cells through a confocal microscope by targeting a group treated with the PINK1 protein and a group not treated with the PINK1 protein as the control group in the arthritis induced animal model according to the exemplary embodiment of the present invention.
Figure 8B:
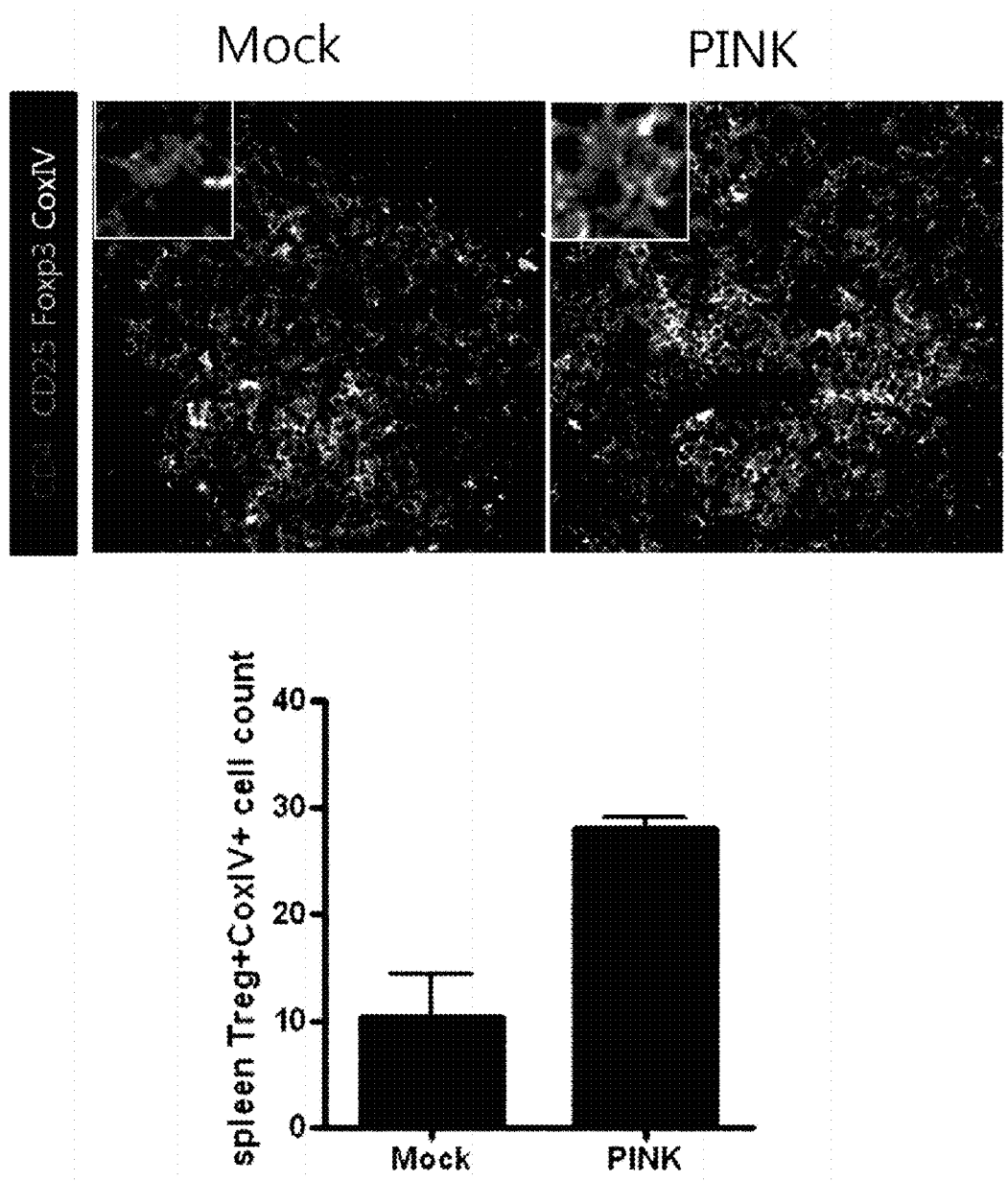

In the group which was injected with the PINK1 protein and the control group which was not injected with the PINK1 protein, as a result of observing the autophagy expressed in the Treg cells through the confocal microscope, in the spleen tissue of the mouse injected with the PINK1 protein, the Treg cells expressing LC3 and coxIV were increased and further, the markers of the Treg cells were activated (see FIG. 8). From the result, it was verified that the PINK1 protein induced activation of autophage of the Treg cells to reinforce the function of the Treg cells and thus may control the Th17 and pathologic cytokines in the autoimmune arthritis.

According to Examples 1 to 8, it can be seen that the PINK1 protein has excellent effects of enhancing the activity of the Treg cells, reducing joint destruction of the articular tissue by inhibiting the activity of Th17, and suppressing arthritis and may be efficiently used for preventing or treating autoimmune disease including arthritis.

For now, the present invention has been described with reference to the exemplary embodiments. It is understood to those skilled in the art that the present invention may be implemented as a modified form without departing from an essential characteristic of the present invention. Therefore, the disclosed exemplary embodiments should be considered from not a limitative viewpoint but an explanatory viewpoint. The scope of the present invention is described in not the above description but the appended claims, and it should be analyzed that all differences within a scope equivalent thereto are included in the present invention.

SEQUENCE LISTING

```
<160> NUMBER OF SEQ ID NOS: 2

<210> SEQ ID NO 1
<211> LENGTH: 580
<212> TYPE: PRT
<213> ORGANISM: Artificial Sequence
<220> FEATURE:
<223> OTHER INFORMATION: PTEN-induced kinase 1 protein

<400> SEQUENCE: 1

Met Ala Val Arg Gln Ala Leu Gly Pro Gly Leu Gln Leu Gly Arg Ala
1               5                   10                  15

Leu Leu Leu Arg Phe Ala Pro Lys Pro Gly Pro Leu Phe Gly Trp Gly
                20                  25                  30

Lys Pro Gly Pro Ala Ala Ala Trp Gly Arg Gly Glu Arg Pro Gly Gln
            35                  40                  45

Val Val Ser Pro Gly Ala Gln Pro Arg Pro Val Gly Leu Pro Leu Pro
        50                  55                  60
```

-continued

```
Asp Arg Tyr Arg Phe Phe Arg Gln Ser Val Ala Gly Leu Ala Ala Arg
 65                  70                  75                  80

Ile Gln Arg Gln Phe Met Val Arg Ala Arg Gly Gly Ala Gly Pro Cys
                 85                  90                  95

Gly Arg Ala Val Phe Leu Ala Phe Gly Leu Gly Leu Gly Leu Ile Glu
            100                 105                 110

Glu Lys Gln Ala Glu Gly Arg Ala Ala Ser Ala Cys Gln Glu Ile
        115                 120                 125

Gln Ala Ile Phe Thr Gln Lys Thr Lys Arg Val Ser Asp Pro Leu Asp
130                 135                 140

Thr Arg Cys Trp Gln Gly Phe Arg Leu Glu Asp Tyr Leu Ile Gly Gln
145                 150                 155                 160

Ala Ile Gly Lys Gly Cys Asn Ala Ala Val Tyr Glu Ala Thr Met Pro
                165                 170                 175

Thr Leu Pro Gln His Leu Glu Lys Ala Lys His Leu Gly Leu Ile Gly
            180                 185                 190

Lys Gly Pro Asp Val Val Leu Lys Gly Ala Asp Gly Glu Gln Ala Pro
        195                 200                 205

Gly Thr Pro Thr Phe Pro Phe Ala Ile Lys Met Met Trp Asn Ile Ser
210                 215                 220

Ala Gly Ser Ser Ser Glu Ala Ile Leu Ser Lys Met Ser Gln Glu Leu
225                 230                 235                 240

Val Pro Ala Ser Arg Val Ala Leu Ala Gly Glu Tyr Gly Ala Val Thr
                245                 250                 255

Tyr Arg Arg Ser Arg Asp Gly Pro Lys Gln Leu Ala Pro His Pro Asn
            260                 265                 270

Ile Ile Arg Val Phe Arg Ala Phe Thr Ser Ser Val Pro Leu Leu Pro
        275                 280                 285

Gly Ala Leu Ala Asp Tyr Pro Asp Met Leu Pro Pro His Tyr Tyr Pro
290                 295                 300

Glu Gly Leu Gly His Gly Arg Thr Leu Phe Leu Val Met Lys Asn Tyr
305                 310                 315                 320

Pro Cys Thr Leu Arg Gln Tyr Leu Glu Glu Gln Thr Pro Ser Ser Arg
                325                 330                 335

Leu Ala Thr Met Met Thr Leu Gln Leu Leu Glu Gly Val Asp His Leu
            340                 345                 350

Val Gln Gln Gly Ile Ala His Arg Asp Leu Lys Ser Asp Asn Ile Leu
        355                 360                 365

Val Glu Trp Asp Ser Asp Gly Cys Pro Trp Leu Val Ile Ser Asp Phe
370                 375                 380

Gly Cys Cys Leu Ala Asp Gln His Val Gly Leu Arg Leu Pro Phe Asn
385                 390                 395                 400

Ser Ser Ser Val Glu Arg Gly Gly Asn Gly Ser Leu Met Ala Pro Glu
                405                 410                 415

Val Ser Thr Ala His Ser Gly Pro Ser Ala Val Ile Asp Tyr Ser Lys
            420                 425                 430

Ala Asp Thr Trp Ala Val Gly Ala Ile Ala Tyr Glu Ile Phe Gly Leu
        435                 440                 445

Ala Asn Pro Phe Tyr Gly Gln Gly Ser Ala His Leu Glu Ser Arg Ser
450                 455                 460

Tyr Gln Glu Ala Gln Leu Pro Glu Met Pro Glu Ser Val Pro Pro Glu
465                 470                 475                 480
```

```
Ala Arg Arg Leu Val Arg Ser Leu Leu Gln Arg Glu Ala Ser Lys Arg
            485                 490                 495

Pro Ser Ala Arg Leu Ala Ala Asn Val Leu His Leu Ser Leu Trp Gly
        500                 505                 510

Glu His Leu Leu Ala Leu Lys Asn Leu Lys Leu Asp Lys Met Ile Ala
            515                 520                 525

Trp Leu Leu Gln Gln Ser Ala Ala Thr Leu Leu Ala Asp Arg Leu Arg
        530                 535                 540

Glu Lys Ser Cys Val Glu Thr Lys Leu Gln Met Leu Phe Leu Ala Asn
545                 550                 555                 560

Leu Glu Cys Glu Ala Leu Cys Gln Ala Ala Leu Leu Leu Ser Ser Trp
                565                 570                 575

Arg Ala Ala Pro
            580

<210> SEQ ID NO 2
<211> LENGTH: 1741
<212> TYPE: DNA
<213> ORGANISM: Artificial Sequence
<220> FEATURE:
<223> OTHER INFORMATION: PTEN-induced kinase 1 protein

<400> SEQUENCE: 2
```

| | | | |
|---|---|---|---|
| atggcggtgc dacaggcact gggcccaggc ctgcagctgg gtcgggcgct gctgctgcgc | | | 60 |
| ttcgcgccca agcccggccc gctgttcggc tgggggaagc ccggccccgc ggcggcctgg | | | 120 |
| ggccgcggag agcgcccagg ccaggtcgta agccccggag cacagcctcg gccggtcggg | | | 180 |
| ctcccctcc cggaccgcta ccgcttcttc cgccagtcgg tagctgggct ggcggcgcgg | | | 240 |
| atccagaggc agttcatggt gcgggcccgg ggcggcgcag gcccttgcgg ccgagcggtc | | | 300 |
| ttcctggcct tcgggctggg gctggggctg atcgaggaga gcaggcgga aggccggagg | | | 360 |
| gccgcctcgg cctgtcagga gatccaggca atttttacac agaaaaccaa gcgcgtgtct | | | 420 |
| gacccactgg acactcgatg ctggcagggc ttccgtctgg aggattatct gatagggcaa | | | 480 |
| gccattggca agggttgcaa tgccgctgtg tatgaagcca ccatgcccac gctgccccag | | | 540 |
| cacctggaaa aggccaaaca ccttggcctt ataggaaagg gccggatgt cgtcctgaag | | | 600 |
| ggagcagacg gggagcaggc tccagggact cccacctttc cctttgccat caagatgatg | | | 660 |
| tggaatatct cggcaggttc ctccagcgaa gccatcttaa gcaaaatgag ccaggagctg | | | 720 |
| gtcccggcaa gccgcgtggc tttggctgga gagtatggag cagttactta cagaagatcc | | | 780 |
| agagatggtc ccaagcagct tgccccacac cctaacatca tccgggtttt ccgcgccttc | | | 840 |
| acctcatctg tgccctcct gccgggggcc ctggctgact atcctgatat gctgccccca | | | 900 |
| cactactacc cagaaggcct gggccacggt cgcacactgt cctcgttat gaagaactac | | | 960 |
| ccctgtaccc tgcgccagta ccttgaggag cagactccca gttctcgcct ggctaccatg | | | 1020 |
| atgaccttgc agttgctgga gggcgtgac catctggttc agcagggcat tgcccatcgg | | | 1080 |
| gatctcaagt ccgacaacat ccttgtggag tgggactcag atggctgtcc ctggctagtg | | | 1140 |
| atctcagact ttggctgctg cctggctgac cagcatgttg gcctgcggct gcctttcaac | | | 1200 |
| agctccagtg tagagcgtgg tggcaatggc tccctgatgg cccctgaggt gtccacagcc | | | 1260 |
| cattctggcc ccagtgcggt aattgactac agcaaagccg ataccctggg ctgtggggcc | | | 1320 |
| atcgcctatg aaatctttgg gcttgccaat cccttctatg ccaaggcag tgcccacctc | | | 1380 |
| gagagccgca gctaccagga agctcagctg cctgagatgc ctgagtcggt gcctccagag | | | 1440 |

| | | | | | |
|---|---|---|---|---|---|
| gcaagacggc | tggtgaggtc | actgctccag | cgagaggcca | gcaagagacc | gtctgcacgc | 1500 |
| ttagctgcaa | atgtgctgca | cttaagcctc | tggggcgagc | atcttctagc | cctgaagaac | 1560 |
| ctgaaattgg | acaagatgat | cgcctggctc | ttgcagcagt | cagcagccac | tctgctggct | 1620 |
| gacaggctga | gagagaagag | ctgcgtggag | acaaagctgc | agatgctgtt | tctggctaac | 1680 |
| ctggagtgtg | aggctctctg | ccaggcagcc | ctcctcctct | cttcctggag | ggcagcccca | 1740 |
| t | | | | | | 1741 |

The invention claimed is:

1. A method for treating an autoimmune disease comprising administering to a patient in need thereof an effective amount of PTEN-induced kinase 1 (PINK1) protein.

2. The method of claim 1, wherein the PINK1 protein has an amino acid sequence represented as SEQ ID NO: 1.

3. The method of claim 1, wherein the PINK1 protein inhibits or decreases the activity of Th17 or promotes or increases the activity of regulatory T cells.

4. The method of claim 1, wherein the PINK1 protein decreases differentiation of osteophage or suppresses infiltration of inflammatory cells.

5. The method of claim 1, wherein the autoimmune disease is selected from the group consisting of rheumatoid arthritis, systemic lupus erythematosus, digestive diabetes, atopic dermatitis, autoimmune encephalomyelitis, asthma and Crohn's disease.

6. A method for preventing or treating an autoimmune disease comprising administering to a patient in need thereof an effective amount of polynucleotide encoding a PINK1 protein.

7. The method of claim 6, wherein the polynucleotide has a base sequence represented as SEQ ID NO: 2.

8. The method of claim 6, wherein the autoimmune disease is selected from the group consisting of rheumatoid arthritis, systemic lupus erythematosus, digestive diabetes, atopic dermatitis, autoimmune encephalomyelitis, asthma and Crohn's disease.

9. A method for preventing or treating an autoimmune disease comprising administering to a patient in need thereof an effective amount of a recombinant vector bound so as to operate polynucleotide encoding a PINK1 protein.

10. The method of claim 9, wherein the autoimmune disease is selected from a group comprised of rheumatoid arthritis, systemic lupus erythematosus, digestive diabetes, atopic dermatitis, autoimmune encephalomyelitis, asthma and Crohn's disease.

\* \* \* \* \*